(12) United States Patent
Kercso et al.

(10) Patent No.: US 6,495,369 B1
(45) Date of Patent: Dec. 17, 2002

(54) HIGH THROUGHPUT MICROFLUIDIC SYSTEMS AND METHODS

(75) Inventors: Joseph E. Kercso, Palo Alto, CA (US); Steven A. Sundberg, San Francisco, CA (US); Jeffrey A. Wolk, Half Moon Bay, CA (US); Andrew W. Toth, Sunnyvale, CA (US); Calvin Y. H. Chow, Portola Valley, CA (US); J. Wallace Parce, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/545,241

(22) Filed: Apr. 7, 2000

Related U.S. Application Data

(62) Division of application No. 09/132,096, filed on Aug. 10, 1998, now Pat. No. 6,132,685.

(51) Int. Cl.[7] .................. G01N 35/02; G01N 35/08; G01N 1/10; G01N 21/00; G01N 31/22; G01N 31/00; G01N 15/06; G01N 33/00; G01N 33/48; B32B 27/04; B32B 27/12; B32B 5/02; B01D 57/02

(52) U.S. Cl. ................. 436/47; 436/180; 436/54; 436/179; 422/68.1; 422/65; 422/66; 422/67; 422/63; 422/55; 422/58; 422/100; 422/82.05; 204/451; 204/601

(58) Field of Search .......... 422/68.1, 63, 65–67, 422/81, 82.05, 99, 100, 52, 55, 58; 436/179, 180; 204/450–451, 600–601; 436/54, 47

(56) References Cited

U.S. PATENT DOCUMENTS

| 4,106,911 A | 8/1978 | Marcelli |
|---|---|---|
| 4,349,275 A | 9/1982 | Ayotte et al. |
| 4,675,300 A | 6/1987 | Zare et al. |
| 4,737,464 A | 4/1988 | McConnell et al. |

(List continued on next page.)

FOREIGN PATENT DOCUMENTS

| EP | 568902 A2 | 11/1993 |
|---|---|---|
| EP | 637998 B1 | 2/1995 |
| EP | 639223 B1 | 2/1995 |

(List continued on next page.)

OTHER PUBLICATIONS

Bao et al., "Ultrmicro enzyme assays in a capillary electroporetic system" *J. Chromatog.* (1992) 608:217–224.

(List continued on next page.)

*Primary Examiner*—Arlen Soderquist
*Assistant Examiner*—Brian R. Gordon
(74) *Attorney, Agent, or Firm*—Stacey Landry; Quine Intellectual Property Law Group, P.C.

(57) ABSTRACT

The invention provides improved systems, devices, and methods for analyzing a large number of sample compounds contained in standard multi-well microtiter plates or other array structures. The multi-well plates travel along a conveyor system to a test station having a microfluidic device. At the test station, each plate is removed from the conveyor and the wells of the multi-well plate are sequentially aligned with an input port of the microfluidic device. After at least a portion of each sample has been input into the microfluidic channel system, the plate is returned to the conveyor system. Pre and/or post testing stations may be disposed along the conveyor system, and the use of an X-Y-Z robotic arm and novel plate support bracket allows each of the samples in the wells to be input into the microfluidic network through a probe affixed to a microfluidic chip. A clamshell structure having a hinged lid can releasably support the chip while providing and/or accommodating the electrical, optical, structural, and other interface connections between the microfluidic device and the surrounding system.

17 Claims, 10 Drawing Sheets

U.S. PATENT DOCUMENTS

| | | | |
|---|---|---|---|
| 4,861,554 A | | 8/1989 | Sakuma |
| 4,908,112 A | | 3/1990 | Pace |
| 4,963,498 A | | 10/1990 | Hillman et al. |
| 4,978,503 A | | 12/1990 | Shanks et al. |
| 5,096,807 A | | 3/1992 | Leaback |
| 5,104,621 A | * | 4/1992 | Pfost et al. ................. 422/100 |
| 5,122,342 A | | 6/1992 | McCulloch et al. |
| 5,126,022 A | | 6/1992 | Soane et al. |
| 5,140,161 A | | 8/1992 | Hillman et al. |
| 5,144,139 A | | 9/1992 | Hillman et al. |
| 5,164,598 A | | 11/1992 | Hillman et al. |
| 5,171,132 A | | 12/1992 | Miyazaki et al. |
| 5,171,534 A | | 12/1992 | Smith et al. |
| 5,188,963 A | | 2/1993 | Stapleton |
| 5,192,405 A | | 3/1993 | Petersen et al. |
| 5,271,724 A | | 12/1993 | van Lintel |
| 5,273,718 A | | 12/1993 | Skold et al. |
| 5,277,556 A | | 1/1994 | van Lintel |
| 5,277,780 A | * | 1/1994 | Kambara ................. 204/603 |
| 5,278,048 A | | 1/1994 | Parce et al. |
| 5,294,795 A | | 3/1994 | Lehtinen et al. |
| 5,296,375 A | | 3/1994 | Kricka et al. |
| 5,304,487 A | | 4/1994 | Wilding et al. |
| 5,324,591 A | | 6/1994 | Georger, Jr. et al. |
| 5,372,695 A | * | 12/1994 | Demorest ................. 204/400 |
| 5,375,979 A | | 12/1994 | Trah |
| 5,380,493 A | | 1/1995 | Chavez et al. |
| 5,384,261 A | | 1/1995 | Winkler et al. |
| 5,395,503 A | | 3/1995 | Parce et al. |
| 5,427,946 A | | 6/1995 | Kricka et al. |
| 5,429,734 A | | 7/1995 | Gajar et al. |
| 5,439,649 A | * | 8/1995 | Tseung et al. ............. 118/300 |
| 5,445,939 A | | 8/1995 | Anderson |
| 5,483,843 A | | 1/1996 | Miller et al. |
| 5,486,335 A | | 1/1996 | Wilding et al. |
| 5,496,697 A | | 3/1996 | Parce et al. |
| 5,498,392 A | | 3/1996 | Wilding et al. |
| 5,519,635 A | | 5/1996 | Miyake et al. |
| 5,560,811 A | * | 10/1996 | Briggs et al. ............. 204/451 |
| 5,571,410 A | | 11/1996 | Swedberg et al. |
| 5,585,069 A | | 12/1996 | Zanzucchi et al. |
| 5,592,289 A | | 1/1997 | Norris |
| 5,593,838 A | | 1/1997 | Zanzucchi et al. |
| 5,605,662 A | | 2/1997 | Heller et al. |
| 5,614,415 A | * | 3/1997 | Markin ................. 422/65 |
| 5,620,894 A | | 4/1997 | Barger et al. |
| 5,637,469 A | | 6/1997 | Wilding et al. |
| 5,650,075 A | | 7/1997 | Haas et al. |
| 5,654,200 A | | 8/1997 | Copeland et al. |
| 5,658,723 A | | 8/1997 | Oberhardt |
| 5,674,454 A | * | 10/1997 | Karl et al. ................. 206/456 |
| 5,730,850 A | * | 3/1998 | Kambara et al. ........... 204/452 |
| 5,735,387 A | * | 4/1998 | Polaniec et al. ......... 198/465.1 |
| 5,773,298 A | | 6/1998 | Lynggaard et al. |
| 5,780,754 A | | 7/1998 | Karlberg et al. |
| 5,876,670 A | * | 3/1999 | Mitsumaki et al. ........... 422/65 |
| 5,942,443 A | | 8/1999 | Parce et al. |
| 5,955,028 A | | 9/1999 | Chow |
| 5,968,331 A | * | 10/1999 | Kambara et al. ........... 204/450 |
| 5,972,187 A | | 10/1999 | Parce et al. |
| 5,985,215 A | * | 11/1999 | Sakazume et al. .......... 422/100 |
| 5,989,402 A | * | 11/1999 | Chow et al. ............... 204/450 |
| 5,993,746 A | | 11/1999 | Priha et al. |
| 6,027,691 A | * | 2/2000 | Watts et al. ................. 422/64 |
| 6,068,393 A | * | 5/2000 | Hutchins et al. ............. 422/67 |
| 6,086,740 A | * | 7/2000 | Kennedy ................. 204/601 |
| 6,103,193 A | * | 8/2000 | Iwahashi et al. ........... 422/104 |
| 6,103,199 A | * | 8/2000 | Bjornson et al. .......... 204/450 |
| 6,106,781 A | * | 8/2000 | Rosenberg ................. 422/63 |
| 6,117,392 A | * | 9/2000 | Hanawa et al. ............. 422/65 |
| 6,148,878 A | * | 11/2000 | Ganz et al. ................. 141/129 |
| 6,182,719 B1 | * | 2/2001 | Yahiro ............................. 141/1 |
| 6,207,031 B1 | * | 3/2001 | Adourian et al. ........... 204/450 |
| 6,245,297 B1 | * | 6/2001 | Kowallis ................. 422/100 |
| 6,251,343 B1 | * | 6/2001 | Dubrow et al. ............. 422/100 |
| 6,255,116 B1 | * | 7/2001 | Leber et al. ................. 422/100 |
| 6,267,927 B1 | * | 7/2001 | Pomar Longedo et al. . 422/100 |
| 6,299,840 B1 | * | 10/2001 | Watanabe et al. ............. 422/50 |
| 6,306,659 B1 | * | 10/2001 | Parce et al. ................. 436/47 |
| 6,358,471 B1 | * | 3/2002 | Ishihara ................. 422/100 |
| 6,360,792 B1 | * | 3/2002 | Ganz et al. ................. 141/129 |
| 2002/0009391 A1 | * | 1/2002 | Marquiss et al. ............. 422/63 |
| 2002/0009392 A1 | * | 1/2002 | Wolk et al. ................. 422/63 |

FOREIGN PATENT DOCUMENTS

| | | |
|---|---|---|
| GB | 2248891 A | 4/1992 |
| WO | WO 94/05414 | 3/1994 |
| WO | WO 95/12608 | 5/1995 |
| WO | WO 95/27210 | 10/1995 |
| WO | WO 95/27211 | 10/1995 |
| WO | WO 95/33846 | 12/1995 |
| WO | WO 96/04547 | 2/1996 |
| WO | WO 96/14933 | 5/1996 |
| WO | WO 96/14934 | 5/1996 |
| WO | WO 96/15269 | 5/1996 |
| WO | WO 97/02357 | 1/1997 |
| WO | WO 97/22000 | 6/1997 |
| WO | WO 98/00231 | 1/1998 |
| WO | WO 98/05959 | 2/1998 |

OTHER PUBLICATIONS

Bunin et al., "A general and expedient method for the solid–phase synthesis of 1,4–benzodiazepine derivatives" (1992) *J. Am. Chem. Soc.* 114:10997–10998.

Cho et al., "An unnatural biopolymer" *Science* (1993) 261:1303–1305.

Chu et al., "Affinity capillary electrophoresis–mass spectrometry for screening combinatorial libraries" *J. Am. Chem. Soc.* (1996) 118:7827–7835.

Dasgupta et al., "Electroosmosis: A reliable fluid propulsion system for flow injection analysis" *Anal. Chem.* (1994) 66:1792–1798.

Harmon et al., "Mathematical treatment of electrophoretically mediated microanalysis" *Anal. Chem.* (1993) 65:2655–2662.

Harmon et al., "Selectivity in electrophoretically medicated microanalysis by control of product detection time" *Anal. Chem.* (1994) 66:3797–3805.

Harrison et al., "Capillary electrophoresis and sample injection systems integrated on a planar glass chip" *Anal. Chem.* (1992) 64:1926–1932.

Harrison et al., Micromachining a miniaturized capillary electrophoresis–based chemical analysis system on a chip *Science* (1993) 261:895–897.

Jacobson et al., "Effects of injection schemes and column geometry on the performance of microchip electrophoresis devices" *Anal. Chem.* (1994) 66:1107–1113.

Jacobson et al., "High–speed separations on a microchip" *Anal. Chem.* (1994) 66:1114–1118.

Jacobson et al., "Open channel electrochromatography on a microchip" *Anal. Chem.* (1994) 66:2369–2373.

Jacobson et al., "Microchip electrophoresis with simple stacking" *Electrophoresis* (1995) 16:481–486.

Jacobson et al., "Fused quartz substrates for microchip electrophoresis" *Anal. Chem.* (1995) 67:2059–2063.

Jung et al., "Multiple peptide synthesis methods and their applications" *Angew. Chem. Int. Ed. Engl.* (1992) 31:367–383.

Kikuchi et al., "Optical accessible microchannels formed in a single–crystal silicon substrate for studies of blood rheology" *Microvascular Res.* (1992) 44:226–240.

Koutny et al., "Microchip electrophoretic immunoassay for serum cortisol" *Anal. Chem.* (1996) 68:18–22.

Linhares et al., "Use of an on–column fracture in capillary zone electrophoresis for sample introduction" *Anal. Chem.* (1991) 63:2076–2078.

Manz et al. "Miniaturized total chemical analysis systems: A novel concept for chemical sensing" *Sensors and Actuators* (1990) B1:244–248.

Manz et al. "Micromachining of monocrystalline silicon and glass for chemcial analysis systems. A look into next century's technology or just a fashionable craze?" *Trends in Anal. Chem.* (1991) 10(5):144–148.

Manz et al. "Electroosmotic pumping and electrophoretic separations for miniaturized chemical analysis systems" *J. Micromech. Microeng.* (1994) 4:257–265.

Pavia et al., "The generation of molecular diversity" *Bioorgan. Med. Chem. Lett.* (1993) 3(3):387–396.

Ramsey et al. "Microfabricated chemcial measurement systems" *Nature Medicine* (1995) No. 110:1093–1096.

Schmalzing et al., "Solution–phase immunoassay for determination of cortisol in serum by capillary electrophoresis" *Clin. Chem.* (1995) 41(9):1403–1406.

Seiler et al. "Planar glass chips for capillary electrophoresis: Repetitive sample injection, quantitation, and separation efficiency" *Anal. Chem.* (1993) 65:1481–1488.

Seller et al., "Electroosmotic pumping and valveless control of fluid flow within a manifold of capillaries on glass chip" *Anal. Chem.* (1994) 66:3485–3491.

Simon et al., "Peptoids: A modular approach to drug discovery" *Proc. Natl. Acad. Sci. USA* (1992) 89:9367–9371.

Song et al., "Multisample analysis using an array of microreactors for an alternating–current field–enhanced latex immunoassay" *Anal. Chem.* (1994) 66(6):778–781.

Weaver et al., "Gel microdroplets: Rapid detection and enumeration of individual microorganisms by their metabolic activity" *Bio/technology* (1988) 6:1084–1089.

Wiley et al., "Peptidomimetics derived from natural products" *Medicinal Research Reviews* (1993) 13(3)327–384.

Wooley et al., "Ultra–high–speed DNA fragment separations using microfabricated capillary array electrophoresis chips" *Proc. Natl. Acad. Sci. USA* (1994) 91:11348–11352.

Zuckerman et al., "Efficient method for the preparation of peptoides [oligo(N–substituted glycines)] by submonomer sold–phase synthesis" *J. Am. Chem. Soc.* (1992) 114:10646–10647.

* cited by examiner

HIGH THROUGHPUT MICROFLUIDIC SYSTEMS AND METHODS

CROSS-REFERENCES TO RELATED APPLICATIONS

The present application is a divisional patent application of and claims the benefit of priority from U.S. Pat. No. 6,132,685 filed Aug. 10, 1998, the full disclosure of which is incorporated herein by reference.

BACKGROUND OF THE INVENTION

The present invention relates generally to microfluidic systems, devices, and methods. More particularly, the present invention provides structures and methods that are useful for handling and sequentially introducing large numbers of samples into devices having microfluidic channels.

Considerable work is now underway to develop microfluidic systems, particularly for performing chemical, clinical, and environmental analysis of chemical and biological specimens. The term microfluidic refers to a system or device having a network of chambers connected by channels, in which the channels have microscale dimensions, e.g., having at least one cross sectional dimension in the range from about 0.1 $\mu$m to about 500 $\mu$m. Microfluidic substrates are often fabricated using photolithography, wet chemical etching, injection molding, embossing, and other techniques similar to those employed in the semiconductor industry. The resulting devices can be used to perform a variety of sophisticated chemical and biological analytical techniques.

Microfluidic analytical systems have a number of advantages over conventional chemical or physical laboratory techniques. For example, microfluidic systems are particularly well adapted for analyzing small samples sizes, typically making use of samples on the order of nanoliters and even picoliters. The channel defining substrates may be produced at relatively low cost, and the channels can be arranged to perform numerous specific analytical operations, including mixing, dispensing, valving, reactions, detections, electrophoresis, and the like. The analytical capabilities of microfluidic systems are generally enhanced by increasing the number and complexity of network channels, reaction chambers, and the like.

Substantial advances have recently been made in the general areas of flow control and physical interactions between the samples and the supporting analytical structures. Flow control management may make use of a variety of mechanisms, including the patterned application of voltage, current, or electrical power to the substrate (for example, to induce and/or control electrokinetic flow or electrophoretic separations). Alternatively, fluid flows may be induced mechanically through the application of differential pressure, acoustic energy, or the like. Selective heating, cooling, exposure to light or other radiation, or other inputs may be provided at selected locations distributed about the substrate to promote the desired chemical and/or biological interactions. Similarly, measurements of light or other emissions, electrical/electrochemical signals, and pH may be taken from the substrate to provide analytical results. As work has progressed in each of these areas, the channel size has gradually decreased while the channel network has increased in complexity, significantly enhancing the overall capabilities of microfluidic systems.

One particularly advantageous application for microfluidic techniques is to screen collections of large numbers of samples. There has long been a need to rapidly assay numerous compounds for their effects on various biological processes. For example, enzymologists have long sought improved substrates, inhibitors, and/or catalysts for enzymatic reactions. The pharmaceutical industry has focussed on identifying compounds that may block, reduce, or enhance the interactions between biological molecules, such as the interaction between a receptor and its ligand. The ability to rapidly process numerous samples for detection of biological molecules relevant to diagnostic or forensic analysis could also have substantial benefits for diagnostic medicine, archaeology, anthropology, and modern criminal investigations. Modern drug discovery has long suffered under the limited throughput of known assay systems for screening collections of chemically synthesized molecules and/or natural products. Unfortunately, the dramatic increase in the number of test compounds provided by modern combinatorial chemistry and human genome research has overwhelmed the ability of existing techniques for assaying sample compounds.

The throughput capabilities of existing sample handling and assaying techniques have been improved using parallel screening methods in a variety of robotic sample handling and detection system approaches. While these improvements have increased the number of compounds which can be tested by a system, these existing systems generally require a significant amount of space to accommodate the samples and robotic equipment, and the sample handling equipment often has extremely high costs. Additionally, large quantities of reagents and compounds are used in performing the assays, which reagents have their own associated costs, as well as producing significant waste disposal problems. Use of small amounts of test compounds with these existing techniques can increase the errors associated with fluid handling and management due to evaporation, dispensing errors, and surface tension effects.

A high throughput screening assay system using microfluidic devices has previously been described. Published P.C.T. Patent Application No. WO 98/00231, the full disclosure of which is hereby incorporated by reference for all purposes, describes a microlaboratory system which can sequentially introduce a large number of test compounds (typically contained in multi-well plates) into a number of assay chips or microfluidic devices. This advantageous system allows testing of a large number of sample compounds with a compact sample handling arrangement, while the manipulation of picoliter or nanoliter volumes of chemicals can both enhance the speed of each chemical analysis and minimize sample and waste product volumes. Hence, such a microlaboratory system represents a significant advancement for handling and testing large numbers of chemical and biological compounds.

Although the proposed application of microfluidic devices to high throughput screening provides a tremendous increase in the number of sample compounds which can be cost effectively tested, still further improvements would be desirable. In particular, it would be helpful to develop devices and methods which were adapted to efficiently handle the tremendous number of sample compounds that might be tested with such a system. It would be best if these sample handling techniques were flexibly adaptable to the wide variety of analyses that might be performed in a microfluidic screening system. Such sample handling systems should be tailored to take advantage of the strengths of a microfluidic analytical device, while minimizing any limitations of microfluidic analysis, and while accommodating any particular sensitivity of these new structures which might otherwise induce error. Ideally, all of these enhanced capabilities will be provided in a compact, high throughput system which can be produced at a moderate cost.

SUMMARY OF THE INVENTION

The present invention generally provides improved systems, devices, and methods for analyzing a large number of sample compounds. In many embodiments, the samples will be contained in standard multi-well microtiter plates, such as those having 96, 384, 1536, or higher numbers of wells. These multi-well plates will typically travel along a conveyor system between an input stack and an output stack. One or more test stations, each having a microfluidic device, will be disposed along the conveyor system. At the test station, each multi-well plate can be removed from the conveyor, and the wells of the multi-well plate will typically be sequentially aligned with an input port of the microfluidic device. After at least a portion of each sample has been injected into the microfluidic channel system, the plate will be returned to the conveyor system. Pre and/or post processing stations may be disposed along the conveyor system, and the use of an X-Y-Z robotic arm and a novel plate support bracket allows each of the samples in the wells to be accurately introduced into the microfluidic network. This arrangement avoids having to move the microfluidic device or its port between entering of the samples, significantly simplifying the chip interface structure. In the exemplary embodiment, a clamshell structure having a hinged lid releasably supports the chip while providing and/or accommodating the electrical, fluid, optical, structural, and any other interface connections between the microfluidic device and the surrounding high throughput system.

In a first aspect, the present invention provides a system for analyzing a large number of sample compounds. The system comprises a plurality of arrays, each array having a plurality of regions for holding samples. An array transport system translates the arrays sequentially along an array path. At least one microfluidic device will be disposed off of the array path. The microfluidic device has a sample input port and a channel system with a channel cross sectional dimension in the range from about 0.1 $\mu$m to about 500 $\mu$m. A transportation mechanism moves each array from the array path and sequentially aligns the regions of the array with the port of the microfluidic device.

Preferably, a microfluidic device interface structure supports the microfluidic device (and its port) at a fixed position. This interface structure will preferably comprise a clamshell having a lid pivotally coupled to a base so as to restrain the microfluidic device therebetween. A window through the lid or base facilitates optically coupling an optical detection system to the channel system of the microfluidic device for monitoring an optical characteristic of a reaction within a channel system. Electrodes extending from the base or lid can couple an electrical potential source to fluid within the channel system through electrode ports of the microfluidic device for electrokinetically transporting the fluids within the microfluidic channel system.

In the exemplary embodiment, the array comprises multi-well plates, and the transportation system for moving the plates from the conveyor system includes a robot arm having at least two, and preferably three degrees of freedom. Where the plates define a planar array of wells, such a robotic arm allows the port to be selectively aligned with any of the wells (along the X and Y axes), and allows the plate to be lifted to bring the sample within each well into contact with the input port (along the Z axis). By using a plate support bracket which is narrower than the plate, lifting pins adjacent to the conveyor system can engage exposed peripheral portions of the plate's lower edge to transfer the plate between the bracket and the conveyor system. This avoids complex robotic grasping mechanisms supported by the robotic arm. Pre and/or post testing stations may be disposed along the conveyor system. Such stations might include a sample management station, for example, a card reader which enters data from a bar code affixed to each plate so as to identify the samples thereon. Alternatively, reaction stations may be positioned before and/or after the test station, for example, to controllably dilute the samples contained in the wells of a plate prior to testing, for reconstituting test compounds in an aqueous buffer, and the like. The use of a bi-directional conveyor belt and/or programmable transportation mechanisms provides flexibility in defining different testing sequences. For example, a single sample disposed within one well of a plate might be moved back and forth between a dilution station and the test station to provide data at different reaction times, multiple concentrations, and the like.

In another aspect, the present invention provides a system for analyzing a large number of samples. The system comprises a plurality of plates, each plate having an array of wells. A plate conveyor translates the plates along a plate path. At least one test station will be disposed along the plate path. The at least one test station includes a microfluidic substrate having a sample input port in fluid communication with at least one channel with a cross sectional dimension in a range from about 0.1 $\mu$m to about 500 $\mu$m. The test station further includes a plurality of lifting pins to sequentially lift the plates from the conveyor, and a plate transportation mechanism. The transportation mechanism moves the lifted plates from the plate path with at least two degrees of freedom to sequentially align the wells of the plate with the input port of the substrate. The transportation mechanism comprises a rigid plate support bracket that fittingly receives the plate when the plate rests on the bracket.

The present invention also provides a method for testing a large number of samples. The method comprises arranging the samples in a plurality of wells. The wells are disposed in a plurality of plates, and the plates are transported along a plate path. The plates are removed from the path and the wells are sequentially aligned with a fluid inflow port of a microfluidic device. The samples are transferred sequentially from the wells into a channel system, the channel system having a cross sectional dimension in a range from about 0.1 $\mu$m to 500 $\mu$m.

The present invention further provides a system for analyzing a large number of sample compounds. The system comprises a plurality of arrays, each array having a plurality of regions for holding samples. An array transport system translates the arrays sequentially along an array path. A batch process station is disposed along the array path for simultaneously processing the samples of each array while the array will be disposed at the batch station. At least one sample test device will be disposed off the array path. The test device has a sample input port, and a transportation mechanism moves each array from the array path and sequentially aligns the regions of the array with the port of the test device.

In another aspect, the present invention also provides a support structure for robotic manipulation of a plurality of assay samples. The assay samples are disposed in wells of a plurality of plates, each plate having an upper surface and a lower surface with front, back, left, and right edge surfaces extending therebetween. The support structure comprises a beam defining a proximal end and a distal end with an axis therebetween. An upwardly oriented tab near the distal end of the beam inhibits axial movement of the plate when the plate rests on the support structure. A pair of horizontally opposed sidewalls adjacent the proximal end of the beam fittingly receive left and right edge surfaces of the plate when the plate rests on the support structure.

The invention also provides a related method for manipulating a plurality of assay samples. The method comprises distributing the assay samples in wells of a plurality of plates. Each plate has an upper surface and a lower surface with front, back, left and right edge surfaces extending therebetween. The plates are positioned on a support structure such that a beam of the support structure extends from adjacent the front surface of the plate to adjacent the back surface of the plate. An upwardly oriented tab near the distal end of the beam inhibits movement of the plate. The assay samples within the wells of the plate are moved by translating the bracket.

In yet another aspect, the present invention provides a system for analyzing samples. The system comprises a microfluidic device having a channel system with a channel cross sectional dimension in the range from about 0.1 $\mu$m to about 500 $\mu$m. An interface structure supports the microfluidic device, the structure comprising a base and a lid movably coupled to the base so that the microfluidic device will be restrainable therebetween. At least one of the lid and the base define a window. An optical detection system will be optically coupled to the channel system through the window of the interface structure for monitoring an optical characteristic of a reaction within the channel system.

In yet another aspect, the present invention provides a system for analyzing samples. The system comprises at least one microfluidic device having a channel system with a channel cross sectional dimension in the range from about 0.1 $\mu$m to about 500 $\mu$m. A support structure supports the microfluidic device, the support structure including a base and a lid. The lid rotatably engages the base so as to move between an open position and a closed position. At least one electrode will be mounted within the lid. The at least one electrode will extend into the channel system of the microfluidic device when the lid is disposed in the closed position. The at least one electrode will be clear of the microfluidic device (so that the microfluidic device is removable from the support structure) when the lid is in the open position.

In yet another aspect, the present invention provides a system for testing a large number of sample compounds. The system comprises at least one sample array. A sample transfer mechanism distributes the samples from the sample array to a plurality of reusable arrays. An array transport system translates the reusable arrays sequentially along an array path from the sample transfer mechanism. At least one microfluidic device will be disposed along the array path. The device has a sample input port that admits the samples from the reusable arrays into a channel system with a channel cross sectional dimension in a range from about 0.1 $\mu$m to about 500 $\mu$m. A cleaning system will be disposed along the array path for removing the samples from the arrays.

Preferably, the array path defines a closed loop, so that the reusable arrays are loaded with samples, the samples are moved to and tested in the microfluidic device, the tested arrays are cleaned of the tested samples, and the arrays are loaded with new samples continuously. This may allow the use of specialized arrays incorporating electrodes to facilitate electrokinetically introducing the samples into the microfluidic devices. Advantageously, such a reusable array system avoids the waste problems associated with large numbers of disposable multi-well plates when testing libraries of test compounds. Such libraries will typically include at least 1,000 different test compounds, the libraries preferably having at least 10,000 test compounds, and often having over 100,000 different test compounds.

In another aspect, the present invention provides a screening system for screening a large number of test compounds in a screening assay. The system comprises a first sample array or set of sample arrays comprising at least 1,000 different test compounds. Each of the test compounds is disposed in a separate region of the first sample array or set of sample arrays. A dilution system separately samples each of the different test compounds and delivers each of the different test compounds to a different region on a second sample array or set of sample arrays. The second sample array or set of sample arrays comprises a plurality of different regions for retaining a sample. A screening apparatus is provided for contacting each different test compound with a biochemical system, and for monitoring an effect, if any, of the test compound on the biochemical system. A sampling system samples each of the test compounds from the second sample array or set of sample arrays, and delivers each of the test compounds to the screening apparatus. A sample array recycling system removes the different test compounds from the second sample array or set of sample arrays, dries the second sample array or set of sample arrays, and moves the second sample array or set of sample arrays into position to receive test compounds from the dilution system.

DESCRIPTION OF THE SPECIFIC EMBODIMENTS

The present invention provides systems, devices, and methods for handling and introducing large numbers of sample compounds into a channel network of a microfluidic device. In particular, the invention facilitates sequential introduction of a large number of sample compounds into the channel network from a plurality of multi-well plates (or other array structures). The systems of the present invention will find applications in screening large numbers of different compounds for their effects in a wide variety of chemical, and particularly biochemical, systems. Thus, the invention will have applications for general assay screening, in diagnostic and other clinical settings, for pharmacological agent screening, and the like.

Figure 1:
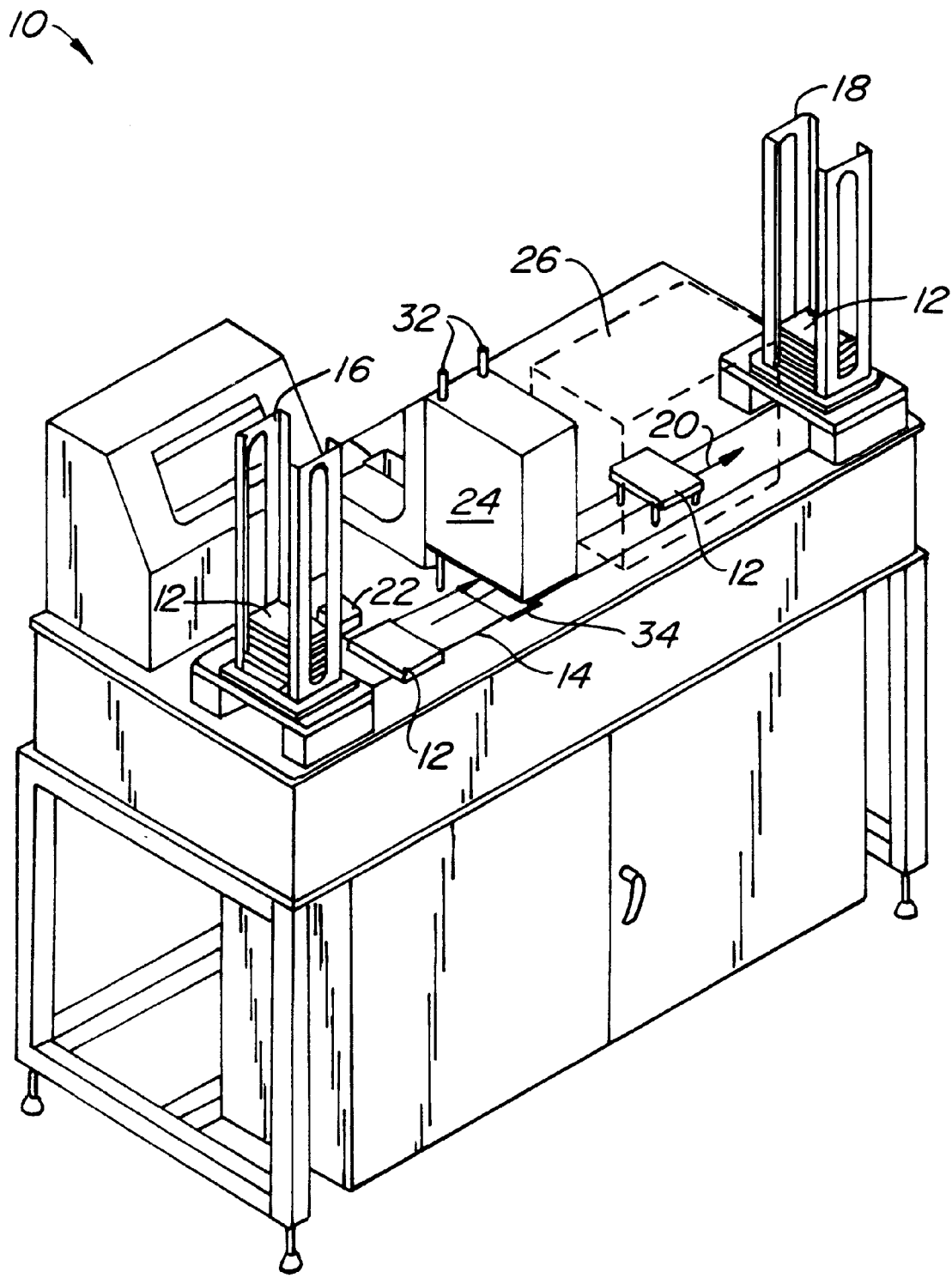
FIG. 1 is a perspective view of a high throughput microfluidic screening system showing the path followed by the plates from an input stack to an output stack, according to the principles of the present invention.

Referring now to FIG. 1, a high throughput screening system 10 generally manipulates samples by translating multi-well plates 12 along a conveyor system 14 from an input stack 16 to an output stack 18 along a plate path 20. As the plates travel sequentially along path 20 they pass through a bar code reader station 22, a dilution station 24, and a test station 26 (shown schematically here as a clear box). At test station 26, plates 12 are moved from path 20, and the samples contained in the wells of the plate are sequentially introduced into the channel network of a microfluidic device.

The description hereinbelow will generally refer to tests conducted on sample liquids. In many instances, the number and/or nature of the liquids to be sampled may generate sample handling problems. For example, in chemical screening or drug discovery applications, libraries of compounds for screening may number in the 1,000's or even in the 100,000's. As a result, such libraries require extremely large numbers of sample plates, creating difficulties in sample storage, manipulation, and identification. Additionally, in some cases, specific sample compounds may degrade, complex, or otherwise possess relatively short active half-lives when stored in liquid form. This could potentially result in suspect results where samples are stored in liquid form for long periods prior to screening.

Accordingly, the present invention provides sampling systems which address these further problems by making use of compounds in an immobilized format. As used herein, "immobilized format" encompasses sample materials provided in a fixed configuration, either by incorporation within a fixed matrix (i.e., a porous matrix, a charged matrix, a hydrophobic or hydrophilic matrix, or the like which maintains the sample at a given location). Immobilized format further encompasses samples spotted and dried upon a given sample matrix. Samples may be applied to the sample matrix by any of a number of known methods, and other immobilization or spotting methods may also be employed. For example, where samples are stable in liquid form, sample matrices may include a porous layer, gel or other polymer material which retain a liquid sample without allowing excess diffusion, evaporation, or the like, but permit withdrawal of at least a portion of the sample material, as desired.

In the exemplary embodiment, samples (whether in an immobilized format or liquid form) will be contained in the wells of multi-well plates 12. Multi-well plates typically comprise an array of blind holes or wells, and are commercially available in a variety of forms. Particularly advantageous multi-well plates include a 96 well clear polymer plate sold by Coming, with an orthogonal 12×8 array of wells. An alternative 384 well plate is commercially available from Genetix, in which the wells are arranged in a 16×24 array. These plates are very roughly 3.5 inches in width, 5 inches in length, and ⅜ inch in height. The present invention will also find applications with a wide variety of alternative plate and sample array structures.

Conveyor 14 preferably comprises a pair of flexible drive belts driven by a shaft of a single motor. In the exemplary embodiment, the position of plates 12 along path 20 is controlled using pins extending upward between the belts. These pins can block progress of plates 12 at dilution station 24, testing station 26, or the like, so that the belts of the conveyor system can run continuously. Alternatively, conveyor system 14 might make use of stepper motors, an arm moveable in linear or polar coordinates, or a wide variety of alternative transportation mechanisms. In the exemplary embodiment using flexible drive belts, the return path for each belt is disposed below an upper surface or deck of high throughput system 10, the belts comprising elastomeric polymer tubes. Conveyor system 14, input stack 16, output stack 18, the conveyor stop pins, and many of the other plate handling components of high throughput system 10 are commercially available through Carl Creative Systems of Harbor City, Calif.

Input stack 16 comprises a commercially available downstacker for lowering plates 12 onto conveyor system 14. Similarly, output stack 18 comprises a commercially available upstacker for removing plates 12 from the conveyor system. These commercially available plate handling modules controllably raise and lower the plates contained therein per instruction signals from a processor, as will be described hereinbelow.

Bar code reader station 22 includes an optical bar code reader oriented towards a back edge of plates 12. The bar codes disposed on the back edge of plates 12 may provide information regarding the specific samples contained in the wells of the plates, or may alternatively comprise a plate identifier so that the sample and/or test parameters are retrieved from a look-up table by the processor. A sample's data might include any or all of the identity of the sample compounds, the quantity, purity, source, or other sample specific information, or may provide test specific information regarding dilution ratios, reaction times, the number or format of samples in the array, or the like. A wide variety of alternative sample management stations may be provided instead of or in addition to bar code reader 22, before and/or after each reaction or test station.

Figure 2:
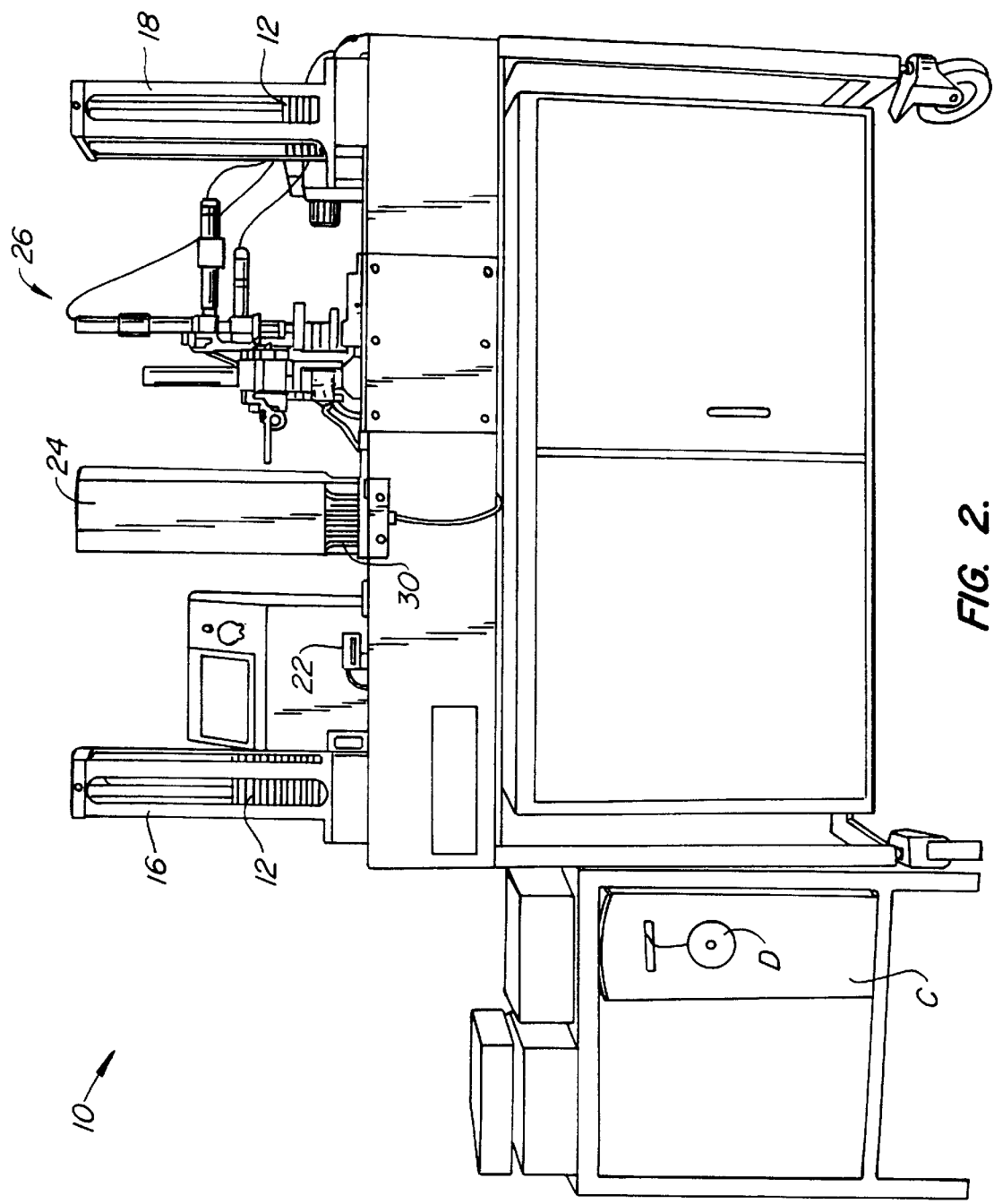
FIG. 2 is a front view of the high throughput screening system of FIG. 1, showing the dilution station, and the test station.

Dilution station 24 comprises a multichannel dispense apparatus for controllably distributing liquids into the wells of plates 12. Where plates 12 include 96 wells, dilution station 24 will typically have a 96 channel dispense head 30, as illustrated in FIG. 2. Similarly, where 384 well plates are used, a 384 channel dispense head may be provided. Alternatively a 96 channel dispense head can distribute liquid into 384 wells (or more) by moving the dispense head relative to the plate (or vice versa). Dispense head 30 can be lowered on supports 32 so that the dispensing tips enter a below deck tip wash module 34, as seen most clearly in FIG. 1. Module 34 can also be used to aspirate buffer for dilution purposes. This allows removal of any contaminants carried on the dispense head tips between dilution of the samples in differing plates.

Dilution station 24 will typically be used to reconstitute the samples in aqueous assay buffers. As microfluidic analysis can make use of very small volumes of sample compounds, the sample may (at least initially) have a starting volume of less than one microliter. Dilution station 24 may variably dilute such volumes with dilution ratios of up to and over 1,000 using the small wells of multi-well plates. Dilution station 24 will typically make use of multichannel pipettor heads, but may alternatively use techniques such as piezoelectric dispensing or pin transfer of small droplets to controllably transfer sub-microliter volumes of liquid.

The inclusion of one or more reaction stations (such as dilution station 24) along a common path 20 with test station 26 provides great flexibility in carrying out screening experiments. For example, the proximity of dilution station 24 with the microfluidic device at the test station allows the user to precisely control and minimize the time delay between reconstitution of test compounds in aqueous buffer and their analysis for binding or inhibitory activity. By flexibly controlling the separation time between dilution and testing, time dependent characteristics of the test compounds (particularly those which are unstable in aqueous environments) can be characterized.

The use of a bi-directional conveyor belt, which might allow a plate 12 to be transferred back and forth repeatedly between a reaction station and a test station, further enhances the flexibility of sample testing. As an example, high throughput system 10 having a single dilution station 24 and a single test station 26 with a bi-directional conveyor belt capable of translating plates back and forth could be used to define a wide variety of different reconstitution and dilution sequences. Starting with a volume of 0.3 microliters of compound in DMSO in each well of multi-well plate 12, one could reconstitute samples into a total volume of 30 microliters (a 100-fold dilution of the compounds, 1% DMSO). These reconstituted samples could then be subjected to a microfluidic assay by moving plate 12 from dilution station 24 to test station 26, after which the plate could be returned to the dilution station for dilution of the tested samples to 300 microliters of total volume (a 1,000-fold dilution of each compound, 0.1% DMSO). The plate could again move to test station 26 for re-assaying at this new concentration. This process can be repeated and/or varied as desired to enhance the predictive value of the data for relative potency.

Figure 3:
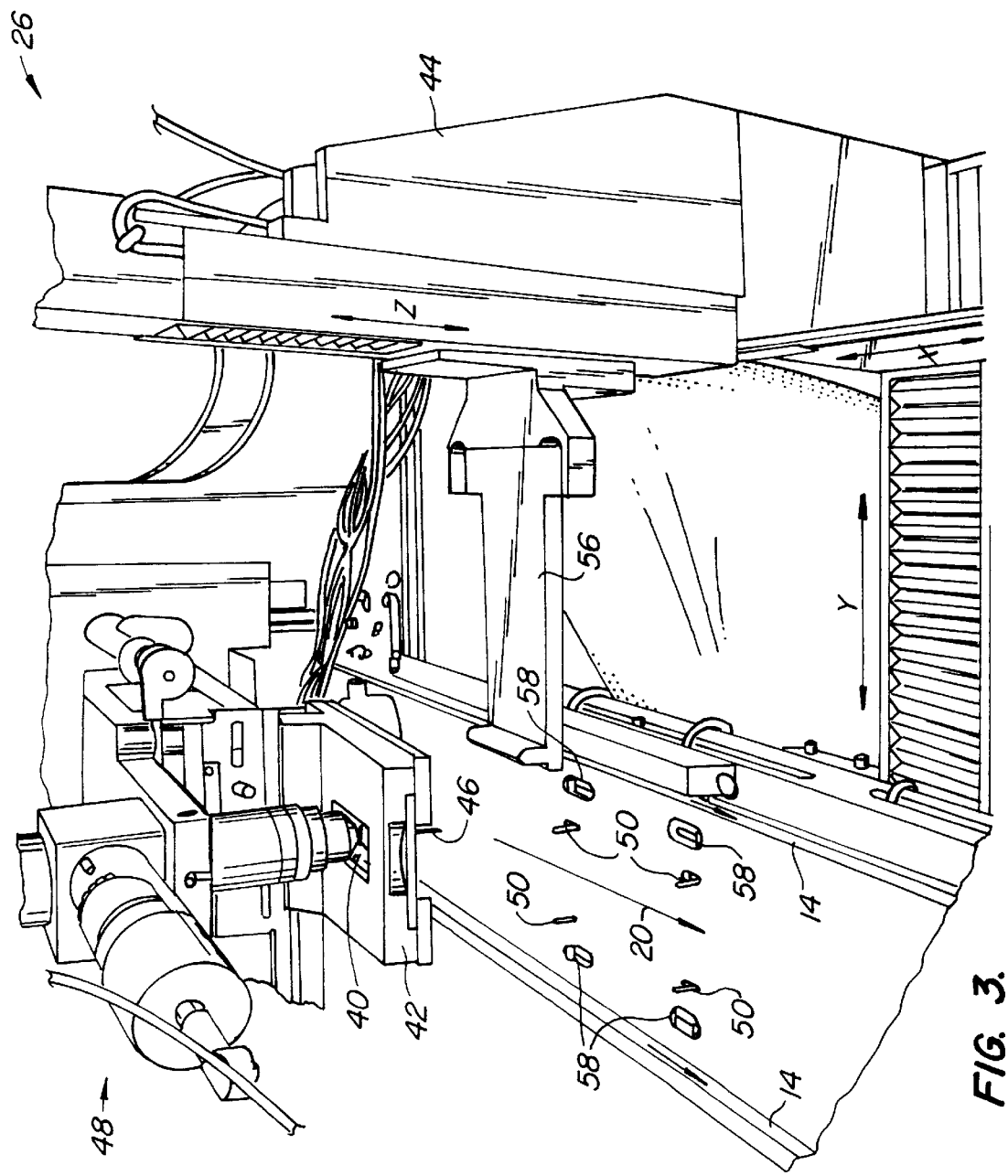
FIG. 3 is a right side detail view of the system of FIG. 1 showing the plate handling equipment of the test station.
Figure 4:
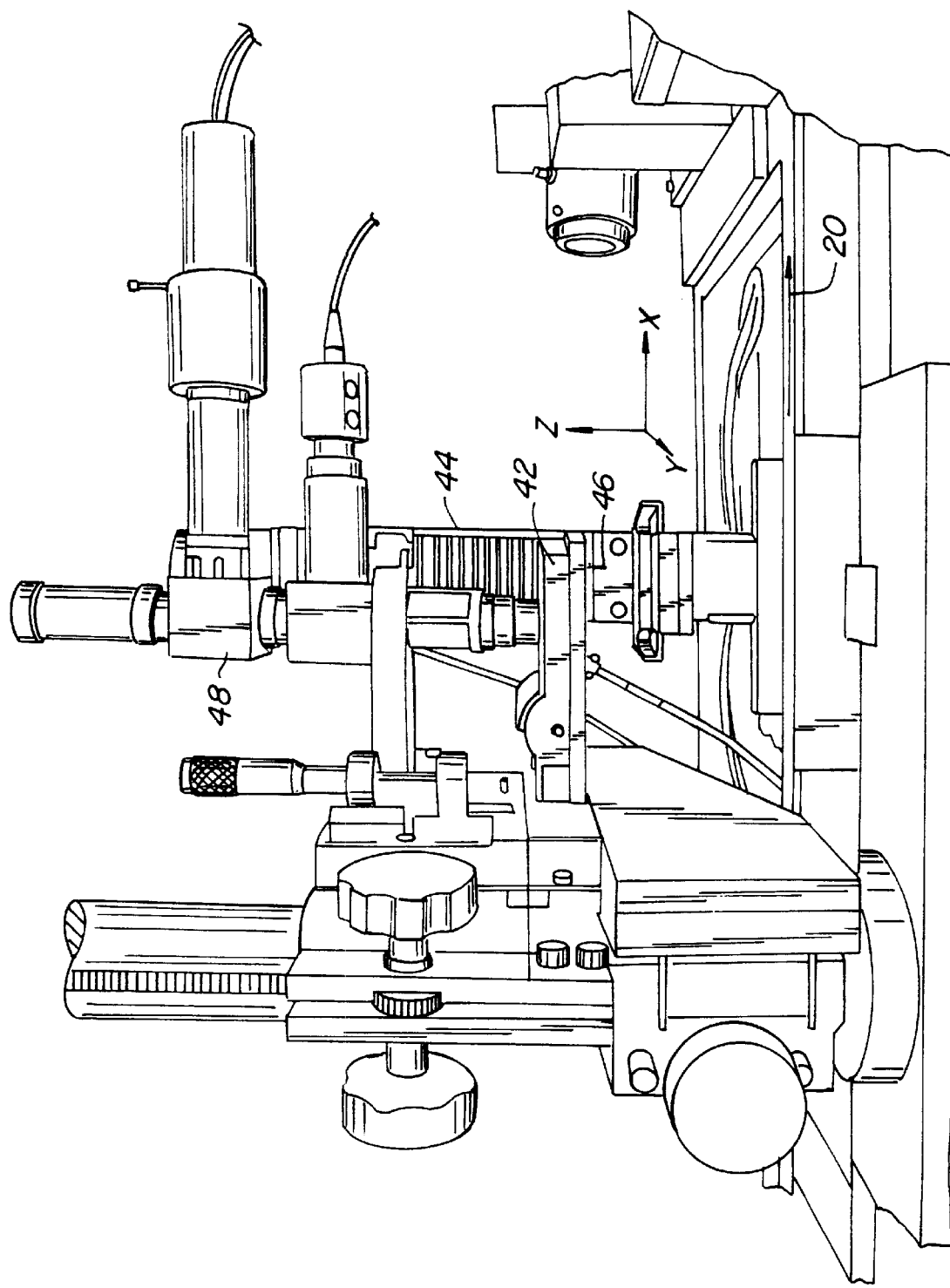
FIG. 4 is a front detail view of the system of FIG. 1, showing a clamshell interface structure containing a microfluidic device.

The structure and arrangement of the components at test station 26 can be understood with reference to FIGS. 3 and 4. Test station 26 generally includes a microfluidic device 40 disposed within a clamshell interface structure 42. X-Y-Z robot arm 44 lifts plate 12 from adjacent plate path 20 and sequentially aligns the wells of the plate with a pipettor 46 extending downward from microfluidic device 40 through a base of clamshell interface 42. Optical detection system 48 optically monitors the assays taking place within the channel network of microfluidic device 40. In alternative embodiments, samples may be introduced from above device 40, detection system 48 may be disposed below the clam shell base, and the like. As can be understood with reference to FIG. 4, the optical detection system 48 and clamshell interface 42 are supported from a front edge of the high throughput system (to one side of path 20), while robotic arm 44 is supported by a back edge of the high throughput system. Stop pins 50 are used to accurately position the plates along path 20 at the test station, allowing the belts of conveyor system 14 to run continuously.

The ability of robotic arm 44 to move plates 12 in three dimensions allows the arm to perform at least three different functions. First, the arm lifts plates in the vertical or Z direction arm to generally transport the plates from adjacent plate path 20 to adjacent microfluidic device 40. This allows the microfluidic device to remain at a fixed location, rather than subjecting the various optical and electrical components that interface with the microfluidic network to repeated movement. Secondly, the robotic arm positions the plate accurately in the X-Y plane to sequentially align the wells of the plate with pipettor 46, thereby allowing the samples in the wells to be sequentially introduced into the channel network of the microfluidic device. Thirdly, once the wells are aligned with the pipettor, the robotic arm can lift the plate to bring the sample in the aligned well into contact with the pipettor, thereby allowing the robotic arm to act as a member of the fluid introduction system. The structure of pipettor 46 and a method for electrokinetically driving the samples into the channel network is described in U.S. Pat. No. 5,958,203 issued to Wallace et al., previously incorporated herein by reference. Alternatively, a wide variety of fluid introduction techniques might be used.

Advantageously, robotic arm 44 fully constrains plate 12 without having to actively grasp the plate using a simple plate bracket 56. The structure and interaction between bracket 56 and plate 12 will be described in detail hereinbelow. To transfer plates 12 between path 20 and the bracket, system 10 will preferably include a plate lifting mechanism disposed at test station 26, as can be understood with reference to FIGS. 3 and 1. Plates 12 are positioned at test station 26 by running conveyor 14 continuously, and by limiting the advancement of the plate along the path using at least the downstream pair of pins 50. Once the plate is accurately positioned along the path, lifters 58 extend upward, lifting plate 12 by engaging a lower surface of the plate adjacent its outer edges. The lifted plate is illustrated most clearly in FIG. 1.

Once the plate is lifted on lifers 58, robotic arm 44 advances bracket 56 between lifters 58, and between the lifted plate and conveyor 14. Once bracket 56 is properly positioned under plate 12, lifters 58 lower the plate onto the bracket, and/or robotic arm 44 raises the bracket upward to engage the plate. Bracket 56 fittingly engages the plate so that the plate can be securely moved both laterally and vertically.

Figure 5:
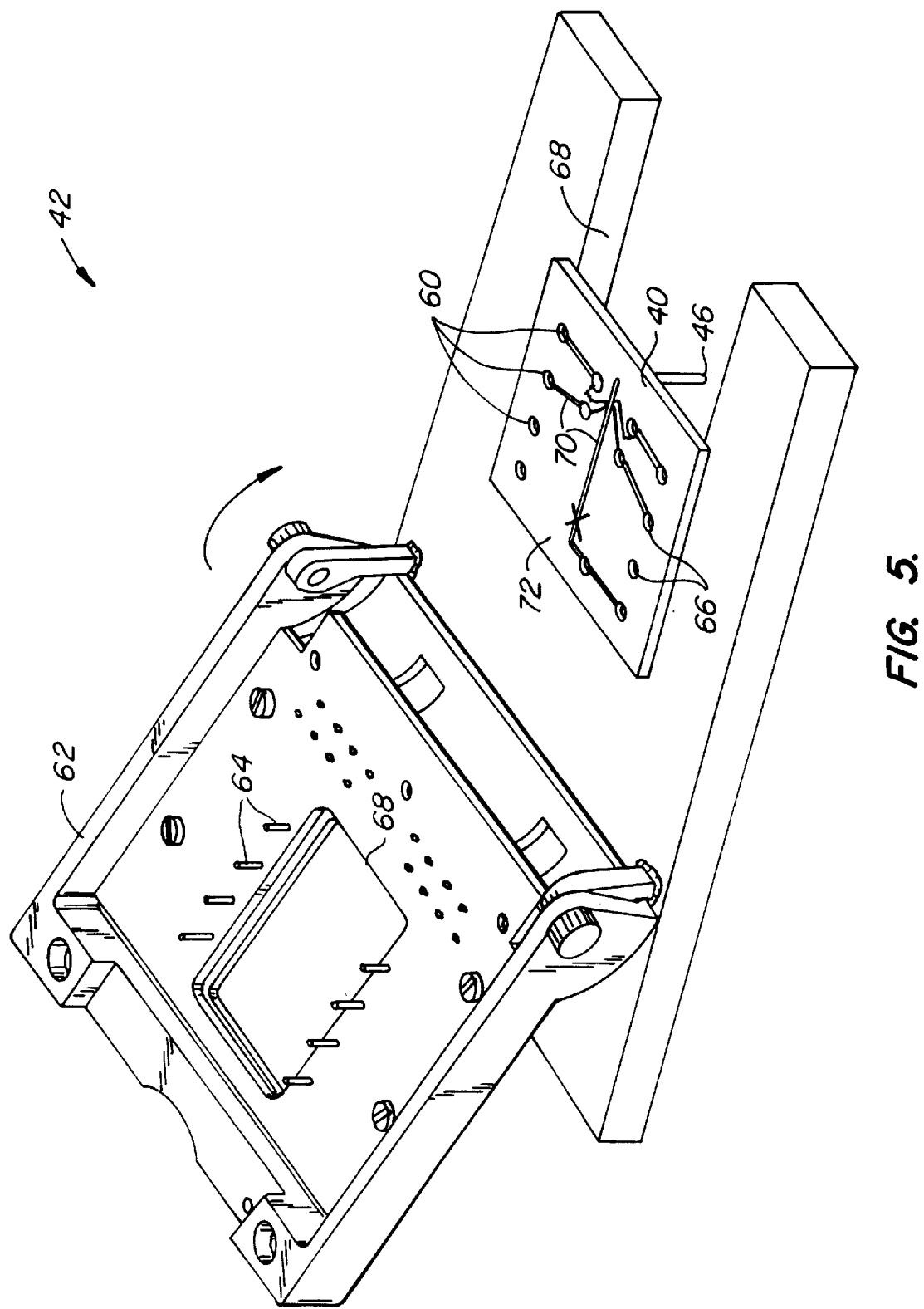
FIG. 5 is a perspective view of the microfluidic device resting on a base of the clamshell support structure, showing a lid of the clamshell support structure in an open position.

Referring now to FIG. 5, clamshell interface 42 generally includes a base 60 and a lid 62 pivotally coupled to the base. The base and lid restrain microfluidic device 40 therebetween, and electrodes 64 mounted on the lid extend into chip wells or ports 66 of the microfluidic device when lid 62 is in a closed position. One or more windows 68 open through base 60 or lid 62 to provide optical access for monitoring the assays in microfluidic device 40. Related structures are described in co-pending U.S. patent application Ser. No. 08/919,707 filed Aug. 29, 1997 (now U.S. Pat. No. 5,989,402), the full disclosure of which is incorporated herein for all reasons.

As shown, microfluidic device 40 is generally fabricated with a planar substrate. Suitable substrate materials are generally selected based on their compatibility with the conditions present in the particular operation to be performed by the device. Such conditions include extremes of pH, temperature, ionic concentration, and application of electrical fields. Additionally, substrate materials are also selected for their inertness to critical components of an analysis or synthesis to be carried out by the system.

Useful substrate materials include glass, quartz, and silicon, as well as polymeric substrates, e.g., plastics. In the case of polymeric substrates, the substrate materials may be rigid, semi-rigid, or non-rigid, opaque, semi-opaque, or transparent, depending on the use for which they are intended. For example, devices which include an optical or visual detection element will generally be fabricated, at least in-part, from transparent materials so as to allow (or at least facilitate) that detection. Alternatively, transparent windows of, e.g., glass or quartz, may be incorporated into the device for these types of detection elements. Additionally, the polymeric materials may have linear or branched backbones, and may be crosslinked or non-crosslinked. Examples of particularly preferred polymeric materials include, e.g., polymethylmethacrylete (PMMA), polydimethylsiloxanes (PDMS), polyurethane, polyvinylchloride (PVC), polystyrene, polysulfone, polycarbonate, and the like.

Figure 5A:
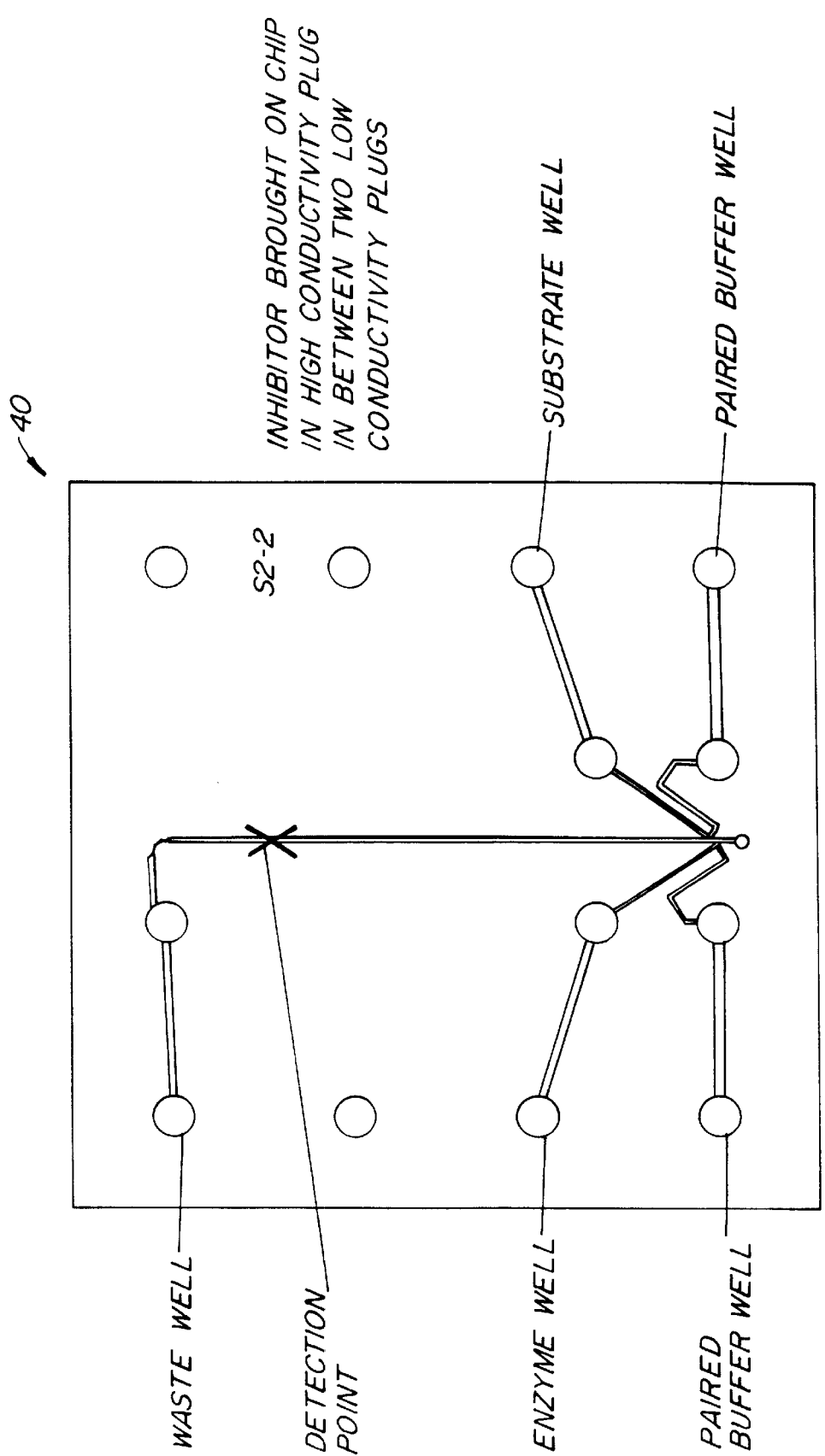
FIG. 5A illustrates an exemplary microfluidic device, showing the channel system and ship wells of ports.

Typically, the substrate will comprise an upper portion through which ports 60 are drilled (or otherwise fabricated), and a lower portion having microfluidic channels 70. The upper portion is bonded to the lower portion so that the channels and ports are in fluid communication. Channels may also be formed in the upper portion as well as, or instead of, the lower portion. In addition to allowing access to the fluid within the channels for electric coupling (using electrode 64 or the like) chip wells or ports 66 may act as reservoirs for fluids to be used in the assaying of the samples. The structure of the substrate and the use of electrokinetics as a transportation mechanism within microfluidic channels is more fully described in Published P.C.T. Application No. 98/00707, and in Published P.C.T. Application No. WO96/04547, the full disclosures of which are incorporated herein by reference. An exemplary microfluidic device 40 is illustrated in FIG. 5A.

A typical chip for assaying biochemical compounds might include ports containing paired buffer solutions, an enzyme port, a waste port, and the like, while the optical detection system may be directed to a detection point 72 along the channel, along a microfluidic reaction chamber, or the like. An exemplary substrate might include channels of varying depths, such as main channels having a depth of 15 $\mu$m, with smaller side channels having a depth of 1.5 $\mu$m. These channels will typically have widths of in the range from about 53 $\mu$m to about 80 $\mu$m, and may be defined using many of the techniques developed for processing of semiconductors, including photolithography, etching, and the like.

As can be seen in FIG. 5, microfluidic device 40 includes at least one pipettor 46 extending below the microfluidic substrate. Pipettor 46 comprises a tubular structure affixed to the substrate of the microfluidic device, and may extend at an angle to the plane of the device substrate (as shown), or may alternatively extend from an edge or corner of the substrate in the plane of the substrate. In such embodiments, clamshell interface device 42 may support microfluidic device 40 so that the plane of the substrate is at an angle from a horizontal reference plane, the substrate optionally being at a vertical orientation so that the side mounted pipettor is vertical to more easily enter the vertical wells of dense multi-well plates. In other embodiments, a wide variety of techniques might be used to introduce samples, including differential pressures, conventional micropipettors, piezoelectric dispenser, pin transfer systems, reservoir/input ports extending through the upper and lower substrate portions, or the like.

While microfluidic device 40 is here illustrated as having a single pipettor, it should be understood that many embodiments of the present invention will include a plurality of pipettors for simultaneously injecting and processing samples in parallel assay channels, thereby providing a higher throughput for the system. One preferred chip configuration might have a linear array of 12 sample probes with nine millimeter or 4.5 mm spacing therebetween, for compatibility with both 96 well and/or 384 well microtiter plates. Such multiplex chip configurations might have each sample pipettors or probes leading to several parallel assay channels, so that multiple assays are run in the same chip. In general, it would be desirable to have common reagents reservoirs feeding all parallel assay channels to simplify loading of the chip.

Design considerations for multiplexed chips will include microfluidics criteria (e.g., flow rates and mixing times, resistance to hydrodynamic flow, filling issues), electrical criteria (e.g., the total resistance of each fluidics pathway, the applied voltages or currents required to generate appropriate electrical fields), fabrication criteria (e.g., yields for making connections between pipettor and microfluidic device 40 might place practical limitations on the multiplexing of a single chip), and assay criteria (e.g., reaction kinetics, protein adsorption issues, etc.).

Although the exemplary embodiment is generally described herein for use with plates having96 or 384 wells, it should be understood that the present invention is adaptable for use with multi-well plates having higher density compound storage formats, including those with 1,536 wells. While the chip need not be multiplexed to densities equivalent to those of the plates, a multiplexed chip having an array of sample input ports (the ports typically aligned as a linear array) with the proper spacing between ports and the proper port size and structure (for example, using a coaxial pipettor/electrode arrangement) can increase throughput and be compatible with one or more high density plate configurations. For example, a linear array of 12 pipettors might be able to input samples from 96, 384, and 1,536 well plates.

To facilitate fabrication of a high density multiplex chip structure, pipettor 46 will optionally incorporate a sample electrode, rather than relying on separate pipettors and sample electrode structures to electrokinetically inject the sample into the sample input port. For example, a layer of platinum may be sputter coated onto the pipettor structure, so that the platinum provides an electrode that is coaxial with the inflow port. Alternatively some or all of plate 12 might be formed of an electrical conductor. For example, plate 12 might comprise a metal (preferably being titanium, stainless steel, aluminum, or the like) so that the entire plate may be used as an electrode. The collection efficiency of the optics might be improved by reducing the thickness of the cover portion of the substrate, the cover portion typically comprising a sheet of glass or other transparent material bonded over the remaining substrate to define the upper surfaces of the channel network. As this cover often includes the openings which define ports 66, an additional well plate extending over the ports may be included to allow the ports to retain sufficient volume to act as reagent reservoirs for sustaining long screening experiments. This additional reservoir plate extending over port 66 might be formed of plastic or the like, and/or might include molded fluid connectors to provide a convenient mechanism for coupling the microfluidic channel network with an external reagent reservoir. One or more of the materials used in fabricating microfluidic device 40 may include surface coatings to reduce protein adsorption, selectively control electrosomatic flow and the like. Other improvements in microfluidic chip technology will be incorporated with these new multiplexed devices, including the use of on chip salt bridges for isolating biological reagents from potential electrochemical degradation near the control electrodes.

Figure 6:
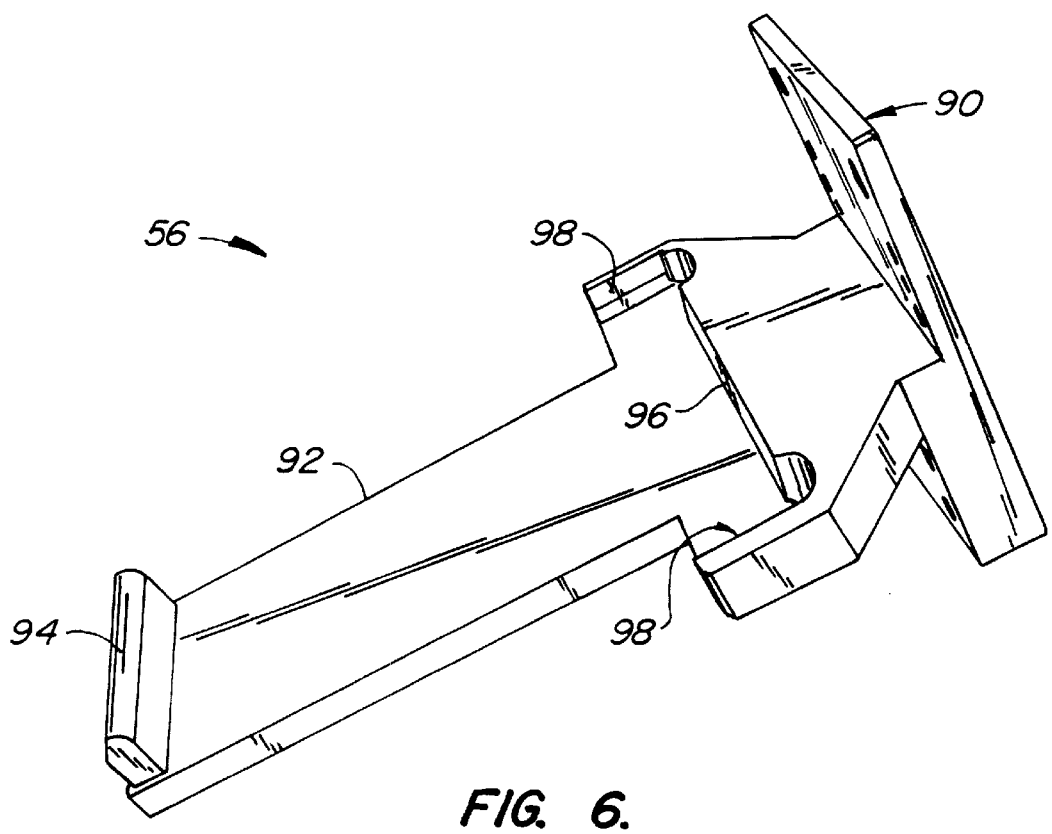
FIG. 6 is a perspective view of a support bracket of the robotic arm which supports the sample plates in the system of FIG. 1.
Figure 7:
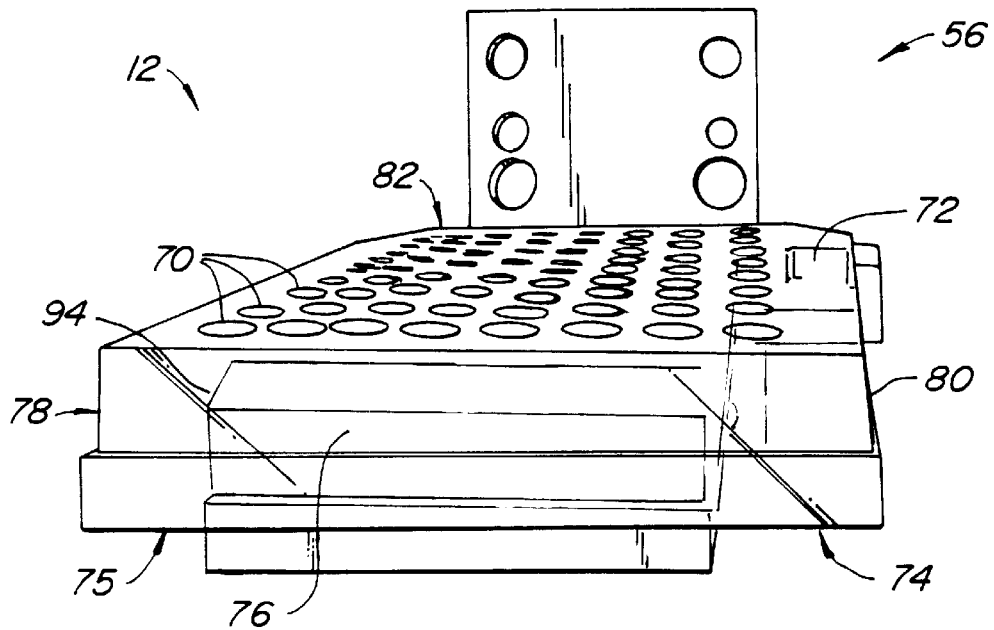
FIG. 7 is a front view showing a sample plate resting on the bracket of FIG. 6.
Figure 8:
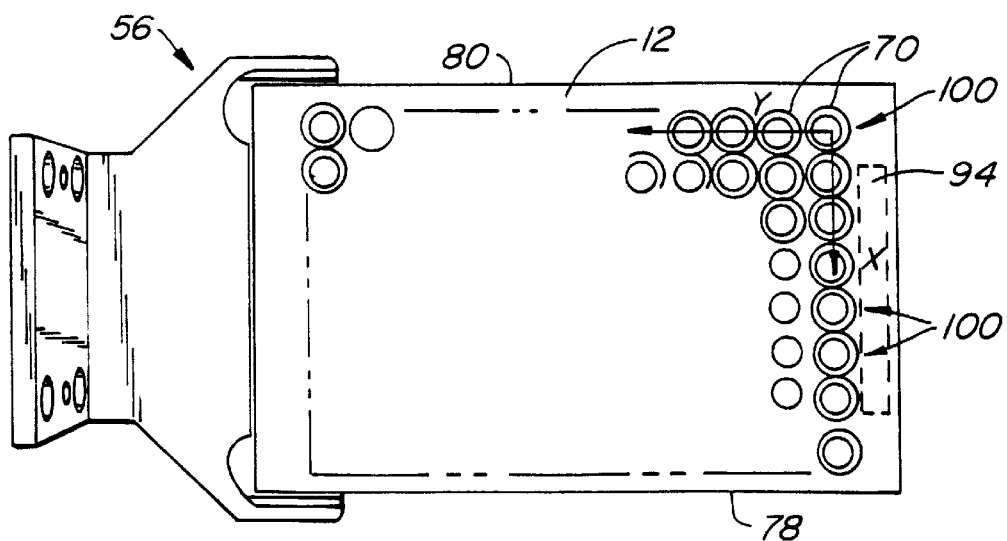
FIG. 8 is a top view of the plate and bracket.

The structure and interaction between bracket 56 and plate 12 can be understood with reference to FIGS. 6–8. In general, each plate 12 includes a plurality of wells 70 defined in an upper surface 72 of the plate. A lower surface 74 will typically define at least one recess disposed between wells 70 and a front edge 76, left and right edges 78, 80 and a back edge 82.

To fully constrain plate 12 when the plate rests on bracket 56, the bracket takes advantage of the generally unused recess between the wells and the edges of the plate. Plate 12 includes a proximal mounting surface 90 and an elongate beam 92 extending distally to an upwardly oriented tab 94. Beam 92 preferably has a width which is significantly less than the width of plate 12 between side edges 78, 80, so that the lower surface 74 of the plate is accessible for lifting pins 58, as discussed above.

Tab 94 limits axial movement of plate 12, recess 75 optionally fittingly receiving the tab between wells 70 and front edge 76. Axial movement of the plate may further be inhibited by an end wall 96 adjacent mounting surface 90. As used herein, the term "tab" encompasses a variety of structure shapes, including pins, posts, etc., that are upwardly oriented at the distal end of the beam.

To laterally constrain plate 12, bracket 56 further includes sidewalls 98 which fittingly receives the side edges of the plate therebetween. Although the plate is here illustrated with its longest dimension aligned parallel to beam 92, it should be understood that bracket 56 may alternatively support the plate with the longest dimension of the plate oriented laterally (or at some other angle relative to the beam). Similarly, while the bracket and system of the present invention are particularly advantageous for use with standard multi-well microtiter plates, it should be understood that the invention could provide benefits for a wide variety of proprietary sample array structures and geometries.

The advantageous use of an X-Y-Z robotic arm in combination with a substantially planar sample array format (such as a standard multi-well plate) can also be understood with reference to FIGS. 7 and 8. Movement of the robotic arm, bracket, and plate along the Y-axis allow a first group 100 of wells 70 to be sequentially aligned with a sample introduction port, such as a pipettor 46. Subsequent movement of the robotic arm, bracket, and plate along the X-axis allows a second group of wells 70 to be aligned with the port, and so on. As each well is aligned with the port, movement of the robotic arm along the Z-axis brings the port into fluid contact with the sample disposed within the aligned well.

Even where a multiplexed chip having a plurality of sample introduction ports is used, the number of introduction ports need not match the number of wells 70 in each group 100. Even where the number of wells in a group does match the number of sample introduction ports, the use of an independently moveable plate transportation system at test station 26 allows sequential introduction of the samples from a plurality of groups without restricting pre or post test batch processes occurring at other stations along the plate path, such as at dilution station 24. An exemplary X-Y-Z robotic positioning system is commercially available from Parker-Hannifin Corporation of Harrison City, Pa. This exemplary arm structure is built up from three independent linear actuators.

Figure 9:
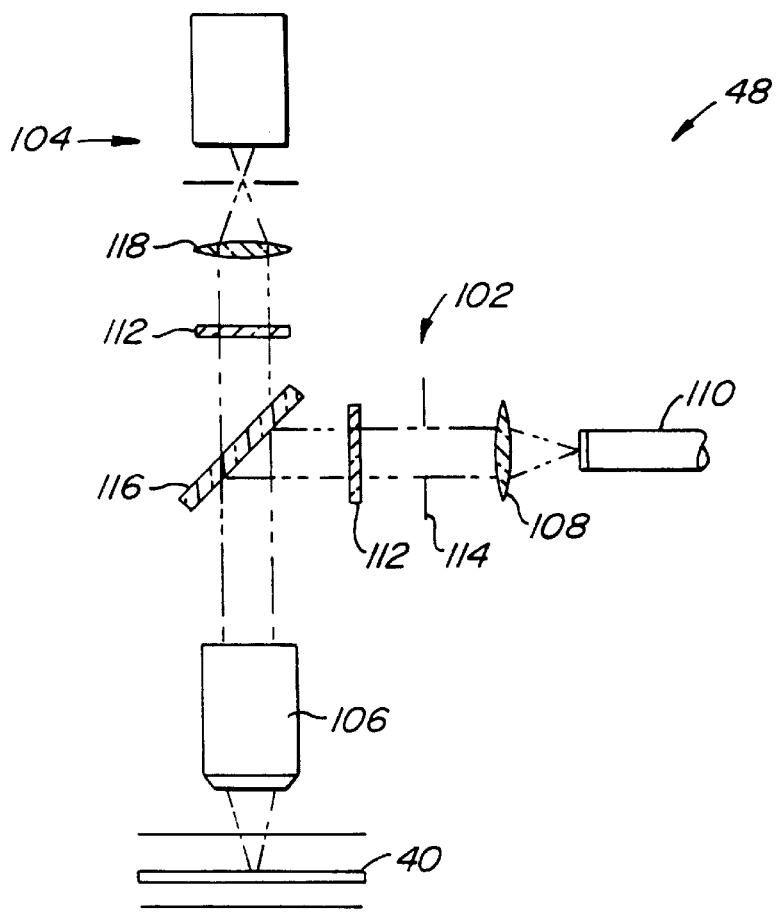
FIG. 9 is a schematic of the optical monitoring system.

A representative optical detection system is schematically illustrated in FIG. 9. To monitor one or more detection points on microfluidic device 40, detection optics 48 generally include an epifluorescence microscope 102 and a photon counting multiplier package 104. More specifically, a 40× aspheric objective 106 and 16× aspheric lens 108 image the detection point toward a 200 im UV-VIS optical fiber 110 through the appropriate filters 112, iris 114, and the like. A dichroic reflector 116 transmits a portion of the optical signal from the objective 106 through a 50 mm focal length lens 118 to the photon counting package. These assemblies are mounted on a vertical column and positioned over the conveyor 14 of high throughput system 10. The mounting structure provides manual X-Y-Z adjustment for focussing and positioning of the optics relative to microfluidic device 40.

Alternative and/or more complex optical detection systems may provide additional capabilities. For example, dual-wavelength excitation and/or detection pathways might be incorporated. It is generally advantageous to arrange the optics in a planar configuration to facilitate stacking optical detection systems for monitoring multiplexed microfluidic devices. The use of appropriate filters, photodiodes, and the like should provide sufficient sensitivity in the near UV range to be used with a wide variety of assays, including, for example, fluoregenic enzyme substrates. In general, variable excitation and emission wavelengths for monitoring a wide variety of biological reactions would be beneficial.

Dual wavelength fluorescence detection (or other detection formats) would be useful in monitoring the position of high salt plugs within the microfluidic channel network. Auto alignment capabilities would be highly beneficial, while rationing of the signal intensity to excitation light intensity could improve instrument stability. The use of optical fiber coupling of the light source to the optical block would enhance the compatibility of the system with laser excitation.

Light tight optical coupling of detection optics 48 with the interface structure housing the microfluidic device may allow screening experiments to be carried out under normal room lighting. Still further alternative detection modes (for example, phase sensitive detection) may also be used to minimize sensitivity to stray room light. Where the microfluidic device is multiplexed, the optical system will generally be capable of accommodating at least the same number of channels as the microfluidic network. For example, to accommodate our preferred multiplexed microfluidic device having twelve sample introduction ports, the optical system will preferably be capable of simultaneously monitoring twelve channels of optical data.

The use of modular optical components facilitates conversion of high throughput system 10 to alternative detection formats. For example, modules may be built for carrying out fluorescence polarization measurements, time resolved fluorescence measurements, CCD imaging, chemiluminescence or bioluminescence measurements, or the like.

A method for using high throughput system 10 will now be described with reference to FIGS. 1–4. The methods of the present invention will generally be performed at least in-part under the direction of a computer C per a computer readable (the code optionally being transferred from a storage media such as a disk D). The exemplary embodiment employs a host personal computer (PC) with a Pentium II® microprocessor (commercially available from Intel Corporation) running a visual basic software module to direct the plate handling equipment. A wide variety of alternative conventional or specialized computer systems might also be used. The computer, display, and conventional sub-system components (e.g., flexible and hard disk drives, memory boards, and the like) need not be described or illustrated here.

Prior to initiating a typical screening run, e.g., for an enzyme inhibition assay, microfluidic device 40 will generally be primed with an appropriate running buffer and loaded into clamshell interface structure 42 of high throughput system 10. Any ports 66 which serve as reservoirs can be filled with biological reagents. The detection optics may then be aligned with the detection point on microfluidic device 40, preferably by initiating a flow of the enzyme and fluorogenic substrate. The detection equipment can then be manually adjusted so that the position and focus of the optics maximize the fluorescence signal.

The user will generally input parameters for controlling the system prior to performing the assays. For example, data file header information may be input or transferred to the host computer, together with any codes or inputs for controlling operational voltages and/or currents, injection dwell times, the number of samples per plate, the sampling pattern, or the like. The user will also input parameters for controlling the plate handling robotics. These robotic inputs may include the number of plates to be run, the type of plate being used, the volume of buffer to be dispensed into each well, the number of aspiration/dispense cycles (to control mixing) or the like.

The plates will also be prepared by loading compounds to be tested into the wells prior to initiating the run. In many cases, the test samples will include, for example, inhibitors to be assayed for optimizing inhibition percentages.

Figure 10:
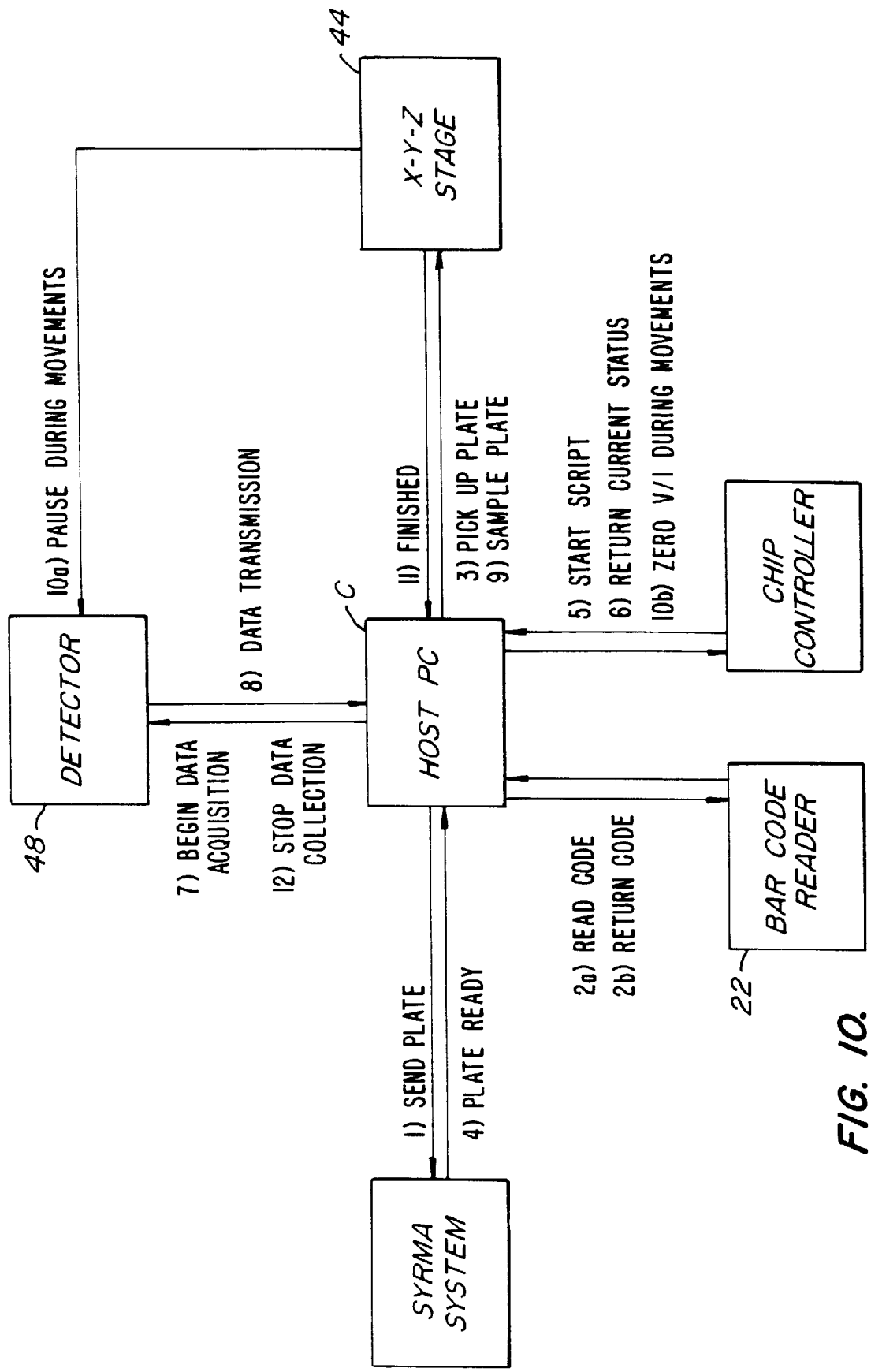
FIG. 10 is a schematic of the information and control system architecture and flow for the system of FIG. 1.

Once the data and plates have been loaded into high throughput system 10, the screening run can be initiated. Referring now to FIG. 10, the host PC will send a signal to the plate handling equipment to download a plate from input stack 16 to conveyor 14. The host PC instructs bar code reader 22 to read the code as the plate passes by (or is held adjacent to) the bar code reader, and the bar code reader returns the read code to the host PC. This code will typically be logged into a data file for the run. In preparation for dilution, dispense head 30 will aspirate the appropriate volumes of assay buffer from a buffer reservoir located below the deck of system 10. Pins can be used to hold plate 12 in position at dilution station 24, and the dispense head then deposits the assay buffer in the wells so as to reconstitute the samples.

After the pins adjacent dilution station 24 lower to allow the plate to advance to test station 26, the plates are held in position at the test station using an additional pair of stop pins. Lifters 58 lift plate 12 off conveyor 14, and the host PC C sends a signal to robotic arm 44 to pick up the lifted plate. As the plate is lifted (and/or during testing of the samples) dispense head 30 can be lowered and rinsed in buffer below the deck system 10, and the dispense head can also aspirate for the next dispense.

Once the system has the plate lifted and ready to be picked up by the robotic arm, the host PC can send a signal to the chip controller to start the chip operating script. The chip controller will return a signal to the host PC regarding the status of the chip operation. The host PC can further send a signal to the optical detection system to begin acquisition of data, with the resulting data signal returning to the host PC.

Robotic arm 44 lifts and sequentially positions the samples within the wells in fluid contact with the pipettor of microfluidic device 40. The microfluidic device draws in material only while the samples are in position, the chip controller and optical detection system both pausing between samples during movements of the robotic arm. The plate is repositioned beneath the chip to sequentially sample all of the desired compounds. Once all compounds have been sampled, the plate is returned to the conveyor belt and moves to upstacker 18. This cycle is repeated for the specified number of plates, typically with plates being simultaneously processed and/or moved by robotic arm 44, conveyor 14, stacks 16, 18, dilution station 24, and test station 26.

While the test is underway, fluorescence data is stored, and this data can be subsequently processed to identify the regions of the spectrum that contain information about the samples. Fluorescence intensities can be quantified for the regions of interests, and can be compared to positive controls so as to calculate the desired test results, for example, percent inhibition. Percent inhibition data could then be correlated with the particular well number (and the sample contained therein) on the multi-well plate.

The throughput of high throughput system 10 is determined by a number of factors. The total injection time for importing samples into the microfluidic network, including time for injection of running buffer, the high salt injection times, and the sample injection time may determine the dwell time of each sample at the fluid input port. These times should be adjusted to maximize throughput, while still maintaining well resolved sample plugs. The overhead or delay time associated with robotically positioning the multi-well plates during the injection cycle may also have a significant impact on throughput. The total robotic overhead time will typically be less than about 5 seconds per injection cycle, ideally being 3.5 seconds or less. Of this total, repositioning the plate to align the port with a sequential well will generally take less than a second. The delay associated with moving sequential plates between conveyor 14 and the microfluidic device will have some effect on this total robotic overhead, although this delay can be minimized by using 384 well or higher density microtiter plates, as this operation need only be performed on a per plate basis (rather than per sample).

To enhance throughput, the control hardware and software, together with the chip interface structure, could be modified to accommodate multiplexed microfluidic devices, as described above. These modifications include adaptations to accommodate the physical dimensions of a larger, multiplexed chip, as well as the circuitry to control voltage and/or current electrically coupled with a greater number of fluidic channels. The control hardware and/or software could be modified to enable real time current and/or voltage sensing and feedback so as to control flow rate, the timing of injections into high salt plugs, and the like. Such a multiplexed microfluidic device controller might also require multiple analog to digital converters to handle multiple channel optical detection. Additional features which might be provided include selective thermostatic temperature control of the microfluidic device (throughout, for example, at least the range from about 25 to 37° C.), refrigeration of off-chip biological reagent reservoirs (for example, down to about 4° C. or less), and improved evaporation control for manually loaded chip reservoirs.

Additional software features which might be incorporated into the computer codes directing system 10 will preferably provide convenient, user defined protocols for synchronized switching of currents and voltages within microfluidic device 40. Synchronized positioning of the robotic arm, plate handling equipment, and fluorescence data acquisition will also ideally be provided. Control will generally be enhanced by improved techniques for more accurate reading of current and voltage, including the use of high read out rates. A wide variety of data system architectures might be used with system 10, for example, use of alternative analog to digital converter arrangements for handling of data acquisition.

In addition to the software enhancements for handling multiplexed microfluidic devices and systems, additional software modules might be implemented to provide real time data processing (e.g., signal processing algorithms might be run to identify regions of interest or to quantify fluorescence intensities or peak areas in regions of interest, correlate quantitative data with a particular sample within the multi-well plate, to calculate percent of inhibition provided by a sample, and/or provide positive controls of the assay). Real time voltage and/or current sensing and feedback might be used to actively control flow rates, timing of injection into high salt plugs, and the like. Advanced error handling protocols might also be available in real time to, for example, allow continuous monitoring of current to detect blockage of fluid flow within the microfluidic network, allow continuous monitoring of data for positive controls included in the experimental set-up so that the operator can be alerted if the data fall outside of a specified range, or the like. The format of data input and/or output files will preferably be compatible with commercially available database software packages.

Figure 11:
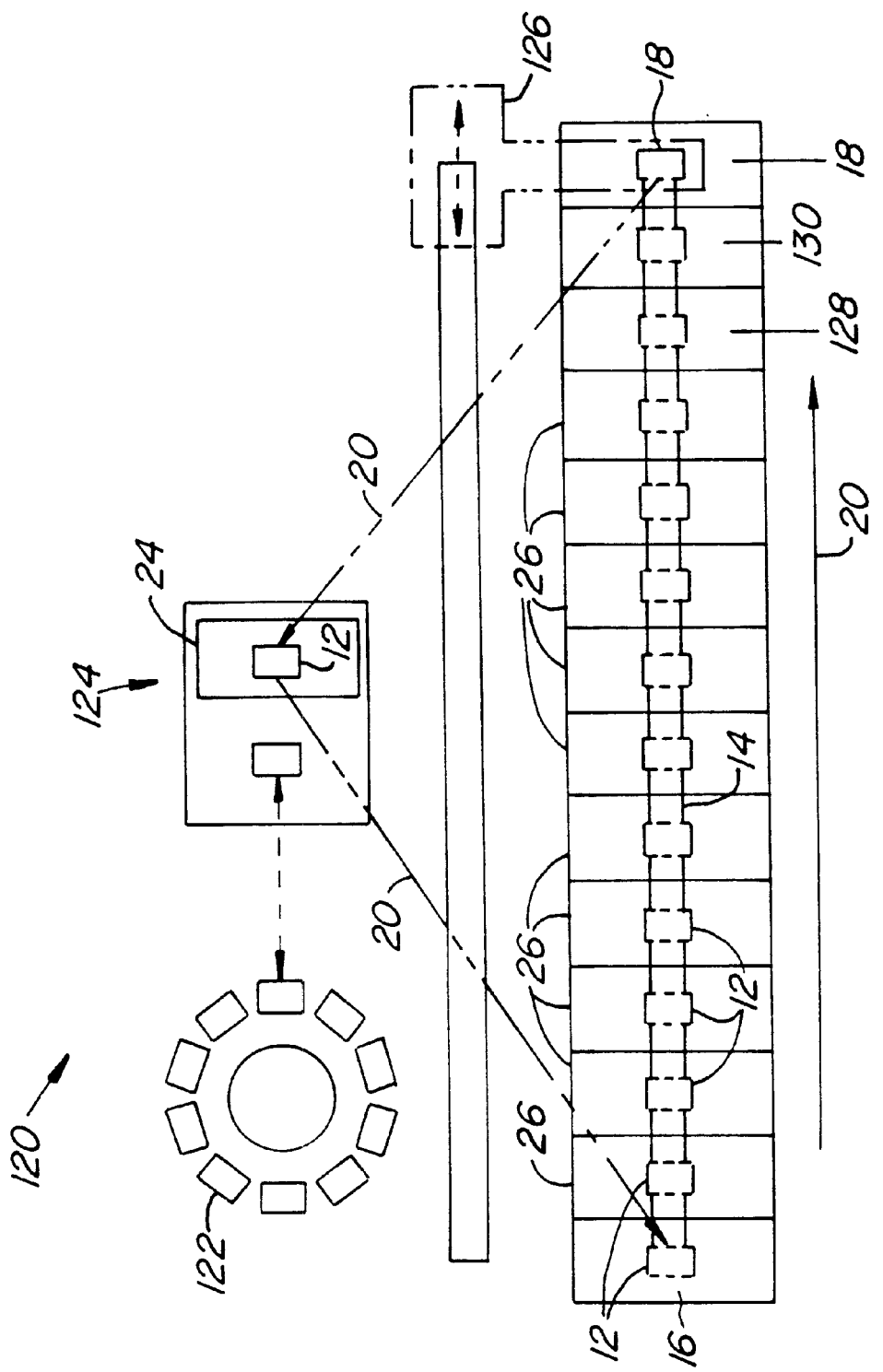
FIG. 11 schematically illustrates a top view of a high throughput system which tests sample compounds that are transported from a sample array to a microfluidic device using reusable plates.

Referring now to FIG. 11, still further modifications of the present invention might be provided to enhance the utility of high throughput system 10. Historically, test tubes were used as reaction vessels, and were then used to transport the resulting compounds to a test site. Standard multi-well microtiter plates can also be used as small reaction vessels when testing large number of sample compounds. Typical reactions might include dilutions, addition of alternative materials, and general mixing. The use of multi-well plates can reduce the overall number of separate reaction vessels, and the logistical complexity of transporting large numbers of samples. Nonetheless, assuming a total of 9,600 samples are to be tested in 96 well plates, and that these unique samples are to be tested at five dilution points each, the total number of plates to be prepared, transported, and tested would be 500.

To still further reduce the number of multi-well plates used when testing large numbers of unique samples, and to avoid the logistical complexity of preparing, maintaining, and handling such a large number of sample plates, a closed loop system 120 includes plates 12 that travel a plate path 20 defining a closed loop. A library of the samples is initially provided on a carousel 122, and the samples are dispensed to the wells of multi-well plate 12 at a sample transfer station 124. The samples are loaded from carousel 122 to plate 12, are reconstituted to the desired dilution point at dilution station 24, and are then transferred to input stack 16 by a robotic arm 126. Alternatively, robotic arm 126 might place plates 12 directly onto conveyor 14. Regardless, the conveyor moves the loaded plate to any of a plurality of test stations 26, at which the plate is removed from the conveyor system and tested.

In the exemplary embodiment illustrated in FIG. 11, ten test stations are provided, so that ten multi-well plates loaded with samples can be tested simultaneously. The test stations may each include a multiplexed microfluidic device, further increasing throughput. Once the samples have been assayed, the plates are returned to conveyor 14, and progress along the path to a wash station 128. Once the samples have been washed from the wells, plates 12 progress to dry station 130, and then proceed to output stack 18. Once again, robotic arm 126 may instead remove multi-well plates 12 from conveyor 14, rather than stacking the plates at the input or output. Regardless, robotic arm 126 transfers the clean plate back to sample transfer station 124.

At sample transfer station 124, the clean and dried plate may receive a new sample from carousel 122, or may alternatively receive at least some of the same samples previously contained by the plate. In the latter case, these samples may be reconstituted to a differing dilution point at aspiration station 24. Hence, plates 12 act as a reusable cache or buffer.

The number of reusable plates will depend on the number of test stations and the transport and process times, rather than the number of unique samples and dilution points to be assayed. As a result, a relatively low number of plates might be used, and the plates may be formed with more exotic materials and/or processes to enhance performance of the system. For example, electrodes and electrical connectors may be provided for applying a potential to the sample within the wells, and to thereby and assist in injecting the sample into the microfluidic channel system, all without significantly impacting the cost of the overall system. Reusable plates may comprise Teflon™, polyethylene, polypropylene, glass, ceramic, metal, or the like. In some embodiments, a metallic multi-well plate may assist in injecting the samples by applying the potential to the plate material, the whole plate acting as an electrode. Such metallic plates will preferably comprise titanium, aluminum, stainless steel, or the like. Alternatively, a multi-well plate may have a conductive layer disposed over a non-conductive substrate. The wells could be formed in a plate of glass, ceramic, a polymer, or the like, over which a layer of metal is sputtered, plated, or otherwise deposited so as to operatively couple an electrical power source to samples disposed in the wells. A wide variety of metal layers might be used, including aluminum, titanium, or the like, with deposition techniques such as those developed for use in the fabrication of integrated circuits and recording media. In some embodiments, a simple metallic foil might be applied over a multi-well plate.

While the exemplary embodiments of the present invention have been described in some detail by way of example and for clarity of understanding, a number of adaptations, modifications, and changes will be obvious to those of skill in the art. As a result, the present invention is limited solely by the appended claims.

What is claimed is:

1. A system for analyzing a large number of sample compounds, the system comprising: a plurality of arrays, each array having a plurality of regions for holding samples; an array transport system for translating the arrays sequentially along an array path; an analysis station comprising at least one microfluidic device disposed off the array path the microfluidic device having a sample input port and a channel system with a channel cross sectional dimension in a range from about 0.1 $\mu$m to about 500 $\mu$m; a transportation mechanism which moves each array from the array path and sequentially aligns each region of the array with the sample input port of the microfluidic device; and a detection system for monitoring a characteristic of the samples in said analysis station.

2. The system of claim 1, further comprising a microfluidic device interface structure supporting the microfluidic device at a fixed position.

3. The system of claim 2, wherein the interface structure comprises a fixed base and a lid, the lid being pivotally coupled to the base so that the microfluidic device is removably restrainable therebetween, at least one of the lid and the base defining a window, and wherein an optical detection system is optically coupled to the channel system through the window for monitoring an optical characteristic of a reaction within the channel system.

4. The system of claim 2, wherein the interface structure further comprises at least one electrode extending fixedly from one of the base and the lid for coupling an electrical potential source to fluid within the channel system.

5. The system of claim 1, wherein the arrays comprise plates and the regions comprise wells wherein a group of the wells on each plate are aligned along a first well alignment axis, and wherein the transportation mechanism can translate the plate with a first degree of freedom along the first well axis to sequentially introduce samples from the group into the sample input port.

6. The system of claim 5, wherein the wells of the plate define an array having a second well alignment axis between a plurality of groups, and wherein the transportation mechanism can translate the plate with a second degree of freedom along the second well axis to introduce samples from the groups into the sample input port.

7. The system of claim 5, wherein the transportation mechanism can move the plate horizontally along the first degree of freedom so that the wells are aligned sequentially with the sample input port, and can lift the plate so that the sample input port extends into the samples within the aligned well, the sample input port comprising a pipettor rigidly coupled to the channel system of the microfluidic device.

8. The system of claim 5, wherein the transportation system comprises a robotic arm having at least two degrees of freedom.

9. The system of claim 1, wherein each array comprises a plate having a top surface defining an upward orientation, two pairs of horizontally opposed edge surfaces, and a lower surface, the regions defining wells and the lower surface defining a recess between the wells and an edge surface, and wherein the transportation mechanism comprises a rigid support bracket having a beam extending from a proximal pair of horizontally spaced sidewalls to an upwardly oriented tab, wherein the recess of the plate fittingly receives the tab and the sidewalls fittingly receive a pair of the edge surfaces when the plate rests on the bracket.

10. The system of claim 9, wherein the plate transport system comprises a conveyor, wherein the transportation mechanism further comprises a plurality of lifting pins disposed along the array path to engage the bottom surfaces of the plates and wherein the pins receive the beam therebetween so as to facilitate transferring the plates between the conveyor and the bracket.

11. The system of claim 1, further comprising a dilution station disposed along the array path before the transportation mechanism for diluting the samples.

12. The system of claim 1, wherein the array path is linear.

13. The system of claim 1, wherein the array path is a loop.

14. A system for analyzing a large number of samples, the system comprising:
   a plurality of plates, each having an array of wells;
   a plate conveyor for translating the plates along a plate path;
   at least one test station disposed along the plate path, the at least one test station comprising;
   a microfluidic substrate having a sample input port in fluid communication with at least one channel disposed within the substrate, the channel having a cross sectional dimension in a range from about 0.1 μm to about 500 μm;
   a plurality of lifting pins to sequentially lift the plates from the conveyor; and
   a plate transportation mechanism which moves the lifted plates from the plate path with at least two degrees of freedom to sequentially align the wells of the plate with the sample input port of the substrate; wherein the transportation mechanism comprises a rigid plate support bracket which fittingly receives the plate when the plate rests on the bracket;
   and a detection system for monitoring a characteristic of the samples in said test station.

15. The system of claim 14, wherein the bracket comprises a beam extending from adjacent a proximal pair of horizontally spaced sidewalls to an upwardly oriented distal tab, wherein the pins receive the beam and tabs therebetween, and wherein a recess of the plate fittingly receives the tab and the sidewalls fittingly receive a pair of horizontally opposed edge surfaces of the plate when the beam lifts the plate.

16. A method for testing a large number of samples the method comprising: Arranging the samples at a plurality of regions, the regions disposed on a plurality of arrays; transporting the arrays along an array path using an array transportation system, removing the arrays from the path and sequentially aligning the regions of the removed array with a sample input port of a microfluidic device using a transportation mechanism so that the samples are transferred sequentially from the regions into a channel system, the channel system having a cross sectional dimension in a range from about 0.1 μm to about 500 μm, and detecting a characteristic of the samples in the microfluidic device.

17. A system for analyzing a large number of samples, the system comprising;
   a plurality of arrays, each array having a plurality of regions for holding samples;
   an array transport system for translating the arrays sequentially along an array path;
   a batch process station disposed along the array path for simultaneously processing the samples of the array;
   an analysis station comprising at least one microfluidic device disposed off the array path, the microfluidic device having a sample input port and a microfluidic channel system;
   a transportation mechanism which moves each array from the array path sequentially aligns each region of the array with the sample input port of the microfluidic device;
   and a detection system for monitoring a characteristic of the samples in said analysis station.

* * * * *

UNITED STATES PATENT AND TRADEMARK OFFICE
CERTIFICATE OF CORRECTION

PATENT NO. : 6,495,369 B1
DATED : December 17, 2002
INVENTOR(S) : Joseph A. Kercso et al.

It is certified that error appears in the above-identified patent and that said Letters Patent is hereby corrected as shown below:

<u>Title page,</u>
Item [74], *Attorney, Agent, or Firm* – "Stacey Landry" should be -- Stacy Landry --

<u>Column 19,</u>
Line 33, "mechanism" should be -- system --.

Signed and Sealed this

Twentieth Day of May, 2003

JAMES E. ROGAN
*Director of the United States Patent and Trademark Office*